United States Patent [19]

Hulin

[11] Patent Number: 5,232,945
[45] Date of Patent: Aug. 3, 1993

[54] 3-ARYL-2-HYDROXYPROPIONIC ACID DERIVATIVES AND ANALOGS AS ANTIHYPERTENSIVES

[75] Inventor: Bernard Hulin, Groton, Conn.
[73] Assignee: Pfizer Inc., New York, N.Y.
[21] Appl. No.: 916,580
[22] Filed: Jul. 20, 1992
[51] Int. Cl.$^5$ ............................................. A61K 31/35
[52] U.S. Cl. .................................. 514/456; 514/374; 514/375; 514/469; 514/571
[58] Field of Search ............... 514/456, 374, 375, 469, 514/571

[56] References Cited

FOREIGN PATENT DOCUMENTS

WO91/19702 12/1991 World Int. Prop. O. .

OTHER PUBLICATIONS

Kaplan, N. M., Clinical Diabetes, 1991, 9, 1–9.
Ferrannini, E. et al., New England Journal of Medicine, 1987, 317, 350–357.
Shen, D. C. et al., Journal of Clinical Endocrinology and Metabolism, 1988, 66, 580–583.

*Primary Examiner*—Leonard Schenkman
*Attorney, Agent, or Firm*—Peter C. Richardson; Gregg C. Benson; Robert T. Ronau

[57] ABSTRACT

A method of using certain 3-aryl-2-hydroxypropionic acid derivatives and analogs in the treatment of hypertension.

13 Claims, No Drawings

3-ARYL-2-HYDROXYPROPIONIC ACID DERIVATIVES AND ANALOGS AS ANTIHYPERTENSIVES

BACKGROUND OF THE INVENTION

The present invention relates to a method of treatment of hypertension in mammals.

Hypertension (or high blood pressure) is a condition which occurs in the human population as a secondary symptom to various other disorders such as renal artery stenosis, pheochromocytoma or endocrine disorders. However, hypertension is also evidenced in many patients in whom the causative agent or disorder is unknown. While such "essential" hypertension is often associated with disorders such as obesity, diabetes and hypertriglyceridemia, the relationship between these disorders has not been elucidated. Additionally, many patients display the symptoms of high blood pressure in the complete absence of any other signa of disease or disorder.

It is known that hypertension can directly lead to heart failure, renal failure and stroke (brain hemorrhaging). These conditions are capable of causing short-term death in a patient. Hypertension can also contribute to the development of atherosclerosis and coronary disease. These conditions gradually weaken a patient and can lead to long-term death.

The exact cause of essential hypertension is unknown, though a number of factors are believed to contribute to the onset of the disease. Among such factors are stress, uncontrolled emotions, unregulated hormone release (the renin, angiotensin, aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus a broad range of β-blockers, vasoconstrictors, renin inhibitors and the like have been developed and marketed as antihypertensives. The treatment of hypertension utilizing these compounds has proven beneficial in the prevention of short-interval deaths such as heart failure, renal failure and brain hemorrhaging. However, the development of atherosclerosis or heart disease due to hypertension over a long period of time remains a problem. This implies that although high blood pressure is being reduced, the underlying cause of essential hypertension is not responding to this treatment.

Hypertension has been associated with elevated blood insulin levels, a condition known as hyperinsulinemia. (See, for example, Kaplan, N. M., Clinical Diabetes, 9, 1–9 (1991), Ferranninni, E., et. al., New England Journal of Medicine, 317, 350–57 (1987), and Shen, D. C., Journal of Clinical Endocrinology, 66, 580-3 (1988).) Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries; while sodium retention increases blood volume. Thus, the lowering of insulin levels in hyperinsulinemics can prevent abnormal vascular growth and renal sodium retention caused by high insulin levels and thereby should alleviate hypertension.

The compounds utilized in the method of the present invention have been disclosed by Hulin, International Patent Publication No. WO 91/19702, which is hereby incorporated by reference. Said compounds were disclosed therein as being useful in the treatment of hyperglycemia and hypercholesterolemia, by virtue of blood glucose level lowering properties and blood cholesterol level lowering properties, respectively.

The present invention provides the surprising and beneficial result that these compounds lower plasma insulin levels after administration to a mammalian subject. More particularly, this insulin level lowering effect is independent of the hypoglycemic properties of the compounds of formulas (I) and (II). Thus, the compounds of formulas (I) and (II) reduce insulin levels in a hyperinsulinemic, normoglycemic patient without affecting the blood glucose levels in said patient. The term "normoglycemic patient" is defined as a patient having normal glucose levels. This lowering of blood insulin levels results in a reduction of blood pressure in a hypertensive mammal.

The new use of the present invention comprises administration of at least one of the foregoing compounds of formulas (I) and (II) to a mammal suffering from hypertension.

SUMMARY OF THE INVENTION

The present invention is directed to a method of reducing blood pressure in a hypertensive mammal which comprises administering to said mammal a blood pressure lowering effective amount of a compound of the formula

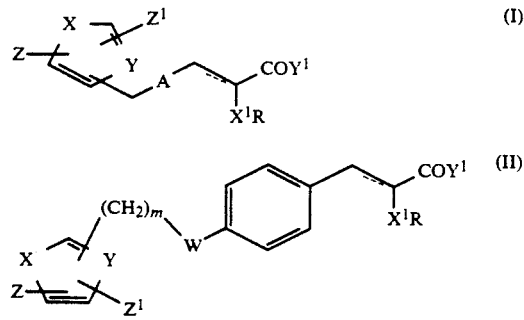

wherein A is

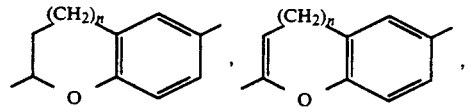

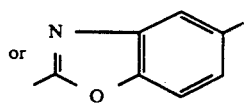

n is 0 or 1;
m is 0, 1 or 2;
represents a bond or no bond;
R is (C$_1$-C$_8$)alkyl, (C$_3$-C$_7$)cycloalkyl, (C$_3$-C$_8$)alkenyl, (C$_3$-C$_8$)alkynyl, phenyl, (C$_7$-C$_8$)phenylalkyl, (C$_2$-C$_8$)alkanoyl, or one of said groups mono- or disubstituted with (C$_1$-C$_3$)alkyl, trifluoromethyl, hydroxy, (C$_1$-C$_3$)alkoxy, fluoro or chloro;

W is O, CO, $CH_2$, CHOH or —CH=CH—;
X is S, O, $NR^2$, —CH=CH—, —CH=N— or —N=CH—;
$R^2$ is hydrogen, $(C_1-C_3)$alkyl, phenyl or benzyl;
Y is CH or N;
Z is H, amino, $(C_1-C_7)$alkyl, $(C_3-C_7)$cycloalkyl, phenyl, or phenyl mono- or disubstituted with $(C_1-C_3)$alkyl, trifluoromethyl, $(C_1-C_3)$alkoxy, phenyl, phenoxy, benzyl, benzyloxy, fluoro or chloro;
$Z^1$ is hydrogen or $(C_1-C_3)$alkyl;
$X^1$ is O, S, SO or $SO_2$; and
$Y^1$ is hydroxy, $(C_1-C_3)$alkoxy, phenoxy, benzyloxy, amino, $(C_1-C_4)$alkanoylamino, $(C_1-C_4)$alkanesulfonylamino, benzenesulfonylamino, napththalenesulfonylamino, di[$(C_1-C_3)$alkyl]aminosulfonylamino, or one of said groups mono- or disubstituted with $(C_1-C_3)$alkyl, trifluoromethyl, hydroxy, $(C_1-C_3)$alkoxy, fluoro or chloro;
or a pharmaceutically-acceptable cationic salt thereof when $Y^1$ is hydroxy;
or a pharmaceutically-acceptable acid addition salt thereof when the compound contains a basic nitrogen atom.

In the preferred compounds, the dotted line (----) represents no bond. The preferred values of A are

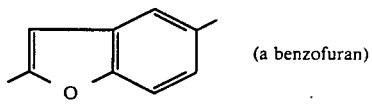
(a benzofuran)

or

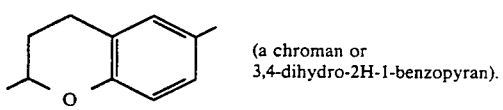
(a chroman or 3,4-dihydro-2H-1-benzopyran).

The preferred values of W are O or CO. In their preferred values, X, Y, Z and $Z^1$ are taken in such manner as to form a 5-methyl-2-phenyloxazol-4-yl group.

In those compounds in which - - - is not a bond, the carbon atom substituted by $X^1R$ and $COY^1$ is asymmetric, such that these compounds can be either racemic or optically active. Resolution of a racemic form into a pair of optically active enantiomers is exemplified below, and the present invention is not to be narrowly construed as limited to the racemic form of these compounds. Similarly, those compounds of the formula (I) wherein the group A contains a saturated ring possess an asymmetric carbon at position 2; and those compounds of the formula (II) contain an asymmetric carbon when W is CHOH.

The expression "pharmaceutically-acceptable cationic salt" is intended to define but not limited to such salts as the alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine) diethylamine, piperazine, tromethamine (2-amino-2-hydroxymethyl-1,3-propanediol) and procaine. An especially preferred such salt is the sodium salt.

The expression "pharmaceutically-acceptable acid addition salt" is intended to define but not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

Also embraced by the present invention are pharmaceutical compositions for use in treating a hypertensive mammal which comprises a blood pressure lowering amount of a compound of formula (I) or (II) and a pharmaceutically-acceptable carrier.

DETAILED DESCRIPTION OF THE PRESENT INVENTION

The compounds of the formulas (I) and (II) of the present invention are readily prepared using conventional chemical processes. In the discussion which follows, the radical R' is defined as follows:

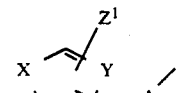

or

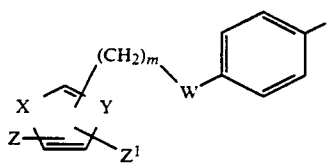

wherein m, A, W, X, Y, Z and $Z^1$ are as defined above.

When the dotted line (----) represents a bond, the compounds of the formula (I) or (II) wherein $Y^1$ is hydroxy and $X^1$ is S are generally prepared from the corresponding aldehyde by the two step sequence:

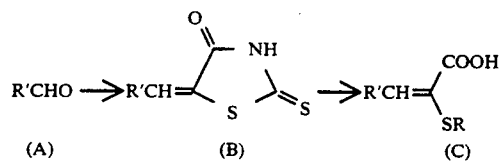

The first step of this sequence is accomplished by condensation of the aldehyde (A) with thiazolidine-4-one-2-thione (rhodanine) in the presence of a secondary amine such as piperidine or pyrrolidine in a reaction inert solvent such as ethanol at a temperature in the range of about 40°–100° C., conveniently at the reflux temperature of the reaction.

As used above and elsewhere herein, the expression "reaction inert solvent" refers to a solvent which does not interact with starting materials, reagents, intermediates or products in a manner which adversely affects the yield of the desired product.

When the dotted line (----) represents a bond, the compounds of the formula (I) or (II) wherein $X^1$ is O are generally prepared by condensation of the above aldehyde (A) with a suitably substituted acetic acid derivative, for example,

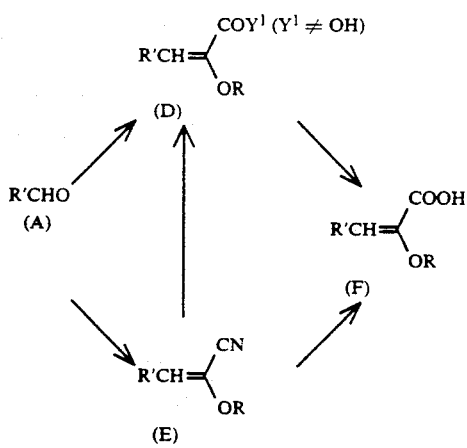

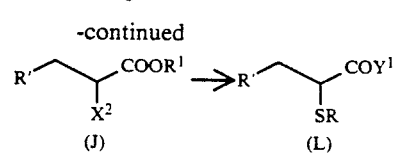

The condensation step is conveniently carried out by irreversibly converting the alkoxy acid derivative, $ROCH_2CN$ or $ROCH_2COY^1$ (in which $Y^1$ is other than OH), to the sodium salt by the action of NaH in a reaction-inert solvent such as dimethylformamide, generally done at a temperature in the range of about 25°–60° C., and then adding the aldehyde and further reacting, generally at a somewhat higher temperature, e.g., 50°–100° C.

If the condensation product is an ester or an amide (D), it can, if desired, be conventionally hydrolyzed, preferably under aqueous basic conditions, to the acid. If the condensation product is a nitrile, it can be conventionally converted to ester, amide or acid, as desired. Specifically exemplified below is the conversion of nitrile to carboxamide, from which both of the expected (E) and (Z) isomers about the double bond are isolated.

The compounds (C) and (F) are further converted to compounds in which $Y^1$ is other than hydroxy by conventional transformations according to which acids are converted to esters, amides and imides. Furthermore, the double bond in such compounds can be conventionally reduced to form compounds of the formulas (I) and (II) wherein the dotted line (----) represents no bond. For example, reduction of the double bond is accomplished by conventional hydrogenation over a noble metal catalyst such as Pd/C, Rh/C or RH(Ph$_3$P)$_3$Cl in a reaction inert solvent such as ethanol generally at temperatures in the range of ambient to 80° C., preferably at moderate pressures, e.g., up to about 125 psig ($8.77 \times 10^4$ Kg/m$^2$) so as not to require expensive and complex high pressure hydrogenation apparatus. However, the presently preferred routes to compounds of the formulas (I) and (II) wherein ---- represents no bond are as detailed below.

Compounds of the formulas (I) and (II) wherein the dotted line (----) represents no bond and $X^1$ is S are generally prepared from the corresponding amine via a two- or three-step reaction sequence:

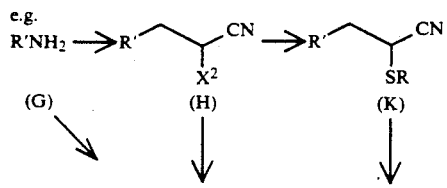

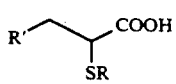

wherein R, R' and $Y^1$ are as defined above, $X^1$ is a nucleophilically displacable group such as I, Cl, Br or $OSO_2CH_3$, and $R^1$ is an ester forming group such as $(C_1-C_3)$alkyl. According to this sequence, the amine (G) is first conventionally diazotized (e.g. with NaNO$_2$/conc.HBr or t-butyl nitrite) in the presence of a copper (II) salt and acrylonitrile or an acrylate ester to form the nitrile (H) or ester (J). This is followed by conventional nucleophilic displacement of the group $X^2$ with RS, with or without conventional concurrent hydrolysis of the nitrile or ester. For example, an alpha-bromo ester (J, $X^2=Br$) is reacted with an excess of an alkali metal salt of a mercaptan or thiolcarboxylic acid (greater than two molar equivalents) in an aqueous solvent such as aqueous dimethylformamide, usually at an elevated temperature, e.g., in the range of 60°–100° C., to form the acid:

$$R' \diagup\diagdown COOH \atop SR$$

On the other hand, the nitrile or ester group is retained intact by reacting a compound (H) or (J) with a mercaptan or thiolcarboxylic acid in the presence of a base such as K$_2$CO$_3$ in an anhydrous reaction inert solvent such as dimethylformamide, generally at lower temperatures, e.g., in the range of about 15°–45° C. Prior to or after nucleophilic displacement, nitrile groups are converted to desired groups —COY$^1$ by conventional methods. For example, compounds wherein $Y^1$ is alkoxy are obtained by contacting the nitrile with dry HCl in an excess of the corresponding alkanol, a reaction usually carried out without additional solvent at a temperature in the range of about 15°–45° C.

Compounds of the formulas (I) and (II) wherein the dotted line (----) represents no bond and $X^1$ is O are generally prepared from the corresponding aldehyde according to the following reaction sequences:

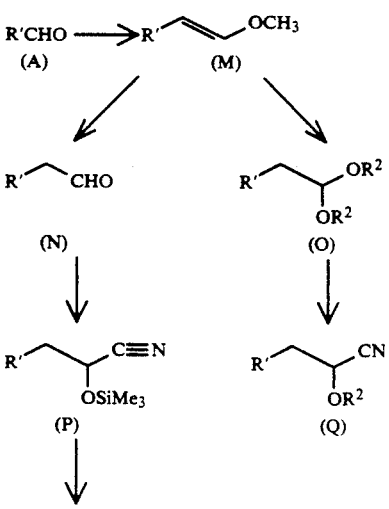

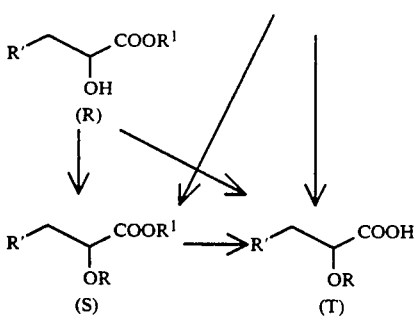

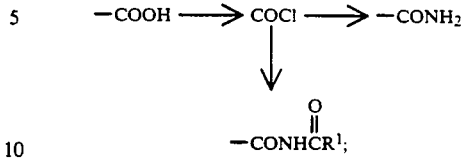

$$-CONHCR^1;$$

and ammonolysis of esters, e.g.,
$-COOR^1 \rightarrow -CONH_2$.

The enol ether (M) is conventionally formed from the aldehyde (A) via the Wittig reaction, using conditions as exemplified in specific examples below. In one further sequence, the enol ether is conventionally hydrolyzed with aqueous acid to form the aldehyde (N), which in turn is reacted with trimethylsilyl cyanide to form the O-trimethylsilylcyanhydrin (P). The latter is conventionally reacted with an alcohol $R^1OH$ in the presence of anhydrous HCl to form the alpha-hydroxy ester (R). When RO is an ester, e.g., acetoxy, the hydroxyester (R) is readily converted to the ester by the action of the appropriate activated acid, e.g., an acid chloride or mixed anhydride, in the presence of at least one equivalent of a tertiary amine, usually in a reaction inert solvent such as tetrahydrofuran, conveniently at or near ambient temperature. When RO is an ether, e.g., ethoxy, the hydroxy ester (R) is reacted with NaH, under scrupulously anhydrous conditions in a reaction inert solvent such as tetrahydrofuran, so as to irreversibly form the sodium salt. The latter is then coupled with a mesylate ester or halide in typical nucleophilic displacement conditions described above, under the same anhydrous conditions to form the ester (S). Alternatively, under hydrous conditions (with at least one molar equivalent of water present), the latter reaction yields the acid (T). In a second further sequence, the enol ether (M) is reacted under anhydrous conditions with an alcohol $R^2OH$ in the presence of a strong anhydrous acid (e.g., p-toluenesulfonic acid) to form the acetal (O), which, upon reaction with trimethylsilyl cyanide, produces the cyanohydrin derivative (Q). The CN group in the latter compound is conventionally converted to the acid (T), e.g., by the action of NaOH in an aqueous solvent, or to the ester (S), e.g., by the action of dry HCl in an excess of an alcohol $R^1OH$.

Many of the compounds of the present invention are alternatively or preferably prepared from preformed compounds having different values of R, $X^1$ and $Y^1$. For example, sulfoxides ($X^1$—SO) are preferably formed from the corresponding sulfide ($X^1$=S) by the action of substantially one molar equivalent of a peroxyacid, conveniently, m-chloroperbenzoic acid. Sulfones ($X^1$=SO_2) are also obtained from the corresponding sulfide, but now generally with an excess (at least 2 molar equivalents) of the peracid. These oxidations are generally carried out in a reaction inert solvent such as tetrahydrofuran, at a temperature generally in the range of about 0°–40° C. Other transformations conveniently carried out to convert one preformed compound of the formula (I) or (II) to another such compound include esterification of acids, e.g.,

conversion of acids to amides or imides, e.g., $$-COOH \longrightarrow COCl \longrightarrow -CONH_2$$

$$\downarrow$$

$$-CONHCR^1;$$
     $\parallel$
     $O$ and ammonolysis of esters, e.g.,
$-COOR^1 \rightarrow -CONH_2$.

Various of these transformations are exemplified below.

It will be readily understood by those skilled in the organic chemical art that in the compounds of the formulas (I) and (II) in which the dotted line (----) represents no bond, the carbon atom bearing the $X^1R$ and $COY^1$ groups is asymmetric and so potentially resolvable into a pair of optically active isomers. Substrates particularly well suited to such resolution are those carboxylic acids of the formulas (I) or (II) wherein $Y^1$ is OH, e.g., by combining the acid with an optically active amine, and separating the resulting pair of diastereomeric salts by fractional crystallization; or by reacting the acid with an optically active alcohol or amine, and separating the resulting pair of diastereomeric esters or amides by chromatography or fractional crystallization, followed by hydrolysis of the separated isomers to yield the desired optically active acids. Such a resolution is exemplified below.

The pharmaceutically-acceptable cationic salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The amines ($R'NH_2$) and aldehydes ($R'CHO$), when not commercially available or known in the prior art, are available by conventional synthetic methods, as exemplified below. For example, the starting aldehydes are generally available as described in WO89/08650, WO89/8651 and WO89/08652 (cited above), and in U.S. Pat. No. 4,725,610; while the amino compounds are most generally available by reduction of the corresponding nitro compounds, as described in that same U.S. Pat. No. 4,725,610.

The present compounds of the formulas (I) and (II) are readily adapted to clinical use as antihypertensive agents. The activity required for this former clinical use is defined by the test procedure described hereinbelow. Male C57BL/6J-ob/ob mice, their lean littermates (ob/+ or ob/?) and C57BL/Ks-db/db mice are supplied at 5-6 weeks of age by Jackson Laboratories (Bar Harbor, Me.) and fed standard rodent diet (Prolab R-M-H 3000 from Agway R, Syracuse, N.Y.) ad libitum. Said mice are allowed to acclimatize for at least 5 days before the studies begin. Male Sprague Dawley rats, 140–160 g, are supplied by Charles River (Kingston, N.Y.), and are fed standard rodent diet (Prolab R-M-H 3000 from Agway R, Syracuse, N.Y.) ad libitum. The rats are allowed to acclimatize for at least 7 days before the studies begin. The drug is administered as a 0.25% solution (weight/volume) in methyl/cellulose by oral gavage. A single daily dose is maintained for 1 to 11 days. Each drug is administered as the sodium salt. (Dosages, however, are expressed as the amount of free acid administered daily). Twenty-four hours after the last dose is administered, blood is collected (25 or 50 μl) by capillary pipette from the retroorbital sinus of ob/ob mice or the tail vein of rats. Said blood is collected for the determination of insulin level. The blood is diluted in 100 μl of heparinized saline or 150 μl of heparinized saline containing 1% (weight/volume) of bovine serum albumin. The solution thus prepared is centrifuged and the supermatant is assayed for insulin. Plasma concentrations in diluted blood samples are calculated assuming a 44% hematocrit. Insulin radioimmunoassay kits were purchased from Cambridge Diagnostics, Billerica, Mass. The interassay coefficient of variation was ≦10%.

The compounds are used in pharmaceutical preparations containing the compound, or pharmaceutically acceptable acid salt thereof, in combination with a pharmaceutically-acceptable carrier or diluent. Suitable pharmaceutically-acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts of the compounds. The injectable solutions prepared in this manner can then be administered intravenously, intraperitoneally, subcutaneously, or intramuscularly, with intramuscular administration being preferred in man.

The present invention is illustrated by the following Examples. However, it should be understood that the invention is not limited to the specific details of these examples. Nomenclature used herein is based on Rigaudy and Klesney, IUPAC Nomenclature of Organic Chemistry, 1979 Ed., Pergammon Press, New York, 1979.

EXAMPLE 1

3-[4-(2-(5-Methyl-2-phenyl-4-oxazolyl)ethoxy)-phenyl]-2-methylthio-2-propenoic Acid 4-[2-(5-Methyl-2-phenyl-4-oxazolyl)ethoxy]-benzaldehyde (Takeda U.S. Pat. No. 4,725,610; 0.5 g, 1.6 mmol), rhodanine (0.21 g, 1.6 mmol) and piperidine (5 drops) were combined in ethanol (10 ml) and heated to reflux for 2 hours. The mixture was cooled and the precipitate filtered (0.35 g, mp 202.5°–203.5° C.). A slurry of this compound (0.25 g, 0.58 mmol) in 15% sodium hydroxide (5 ml) was heated to gentle reflux for 1 hour, then cooled and treated with a solution of methyl iodide (0.16 ml, 2.6 mmol) in methanol (5 ml). After 2 hours stirring at room temperature, the mixture was diluted with ice-water and acidified with 2N hydrochloric acid. The precipitate was filtered and recrystallized from 1:1 ethanol-water (10 ml) (0.11 g, mp 178.5°–182° C.).

Starting from the same aldehyde and using propyl iodide as the reagent, 3-[4-(2-(5-methyl-2-phenyl-4-oxazolyl)ethoxy)phenyl]-2-propylthio-2-propanoic acid was prepared by the same method (gummy solid).

$^1$H NMR (CDCl$_3$, 300 MHz) delta 0.91 (t, J-7.3 Hz, 3H), 1.56 (tq, J=7 Hz, 7 Hz, 2H), 2.38 (s, 3H), 2.76 (t, J=7.3 Hz, 2H), 3.01 (t, J=6.6 Hz, 2H), 4.29 (t, J=6.6 Hz, 2H), 6.92 (d, J=8.9 Hz, 2H), 7.39–7.44 (m, 3H), 7.94–7.99 (m, 4H), 8.05 (s, 1H).

Starting from 4-[3-(5-methyl-2-phenyl-4-oxazolyl)-propionyl]benzaldehyde (WO89/08650), 3-[4-(3-(5-methyl-2-phenyl-4-oxazolyl)propionyl)phenyl]-2-methylthio-2-propenoic acid was prepared by the same method (mp 150°–152° C.).

EXAMPLE 2

3-[4-(2-(5-Methyl-2-phenyl-4-oxazolyl)-phenyl]-2-methylthio-2-propanoic Acid

To a solution of 4-[2-(5-methyl-2-phenyl-4-oxazolyl)ethoxy]aniline (U.S. Pat. No. 4,725,610) (3.7 g, 12.6 mmol) in acetone (50 ml) and methanol (50 ml), cooled to 0° C., was added 48% hydrobromic acid (6.2 ml, 54 mmol), and after 5 minutes a solution of sodium nitrite (1.0 g, 15 mmol) in water (5 ml), dropwise, keeping the temperature below 5° C. After 15 minutes ethyl acrylate (8.6 ml, 79 mmol) was added dropwise, the mixture was warmed to 38° C. and cuprous oxide (0.42 g, 2.9 mmol) was added. The solution was stirred 1 hour at 40° C., then concentrated, diluted with aqueous ammonia and extracted with ethyl acetate (3×30 ml). The combined extracts were washed with water (2×), brine, dried over magnesium sulfate and concentrated. The product, ethyl alpha-bromo-4-[2-(5-methyl-2-phenyl-4-oxazolyl)ethoxy]benzenepropanoate, was isolated by flash chromatography (hexane/ethyl acetate, 4:1) as a yellow oil (1.17 g).

To a solution of ethyl alpha-bromo-4-[2-(5-methyl-2-phenyl-4-oxazolyl)ethoxy]benzenepropanoate (0.20 g, 0.44 mmol) in dimethylformamide (0.5 ml) was added to a solution of sodium thiomethoxide (0.10 g, 1.4 mmol) in water (0.3 ml). The resulting solution was stirred at 80° C. for 16 hours. Water was added and the mixture was acidified with 2N hydrochloric acid and extracted with ethyl acetate (2×). The combined extracts were washed with water (5×) and brine, dried over magnesium sulfate and concentrated to a yellow oil. The product was purified by flash-chromatography (hexane/ethyl acetate, 2:1) and obtained as a yellow gum (60 mg).

$^1$H NMR (CDCl$_3$, 300 MHz) delta 2.19 (s, 3H), 2.36 (s, 3H), 2.88 (dd, J=6 Hz, 14 Hz, 1H), 2.96 (t, J=7 Hz, 2H), 3.16 (dd, J=9 Hz, 14 Hz, 1H), 3.41 (dd, J=6 Hz, 9 Hz, 1H), 4.13 (t, J=7 Hz, 2H), 6.78 (d, J=8 Hz, 2H), 7.11 (d, J=8 Hz, 2H), 7.39–7.41 (m, 3H), 7.92–7.96 (m, 2H).

EXAMPLE 3

Ethyl 3-[4-(2-(5-methyl-2-phenyl-4-oxazolyl)ethoxy)-phenyl]-2-acetylthio-2-propanoate To a solution of ethyl alpha-bromo-4-[2-(5-methyl-2-phenyl-4-oxazolyl)ethoxy]-benzenepropanoate (0.18 g, 0.38 mmol) and thiolacetic acid (75 μl, 1.05 mmol) in dimethylformamide (2 ml) was added potassium carbonate (0.15 g, 1.05 mmol). After stirring overnight at room temperature, the mixture was poured into water and acidified with 1N hydrochloric acid, then extracted with ethyl acetate (3×). The combined extracts were washed with water (5×) and brine, dried over magnesium sulfate and concentrated to a yellow oil (0.11 g).

$^1$H NMR (CDCl$_3$, 300 MHz) delta 1.18 (t, J=7 Hz, 3H), 2.31 (s, 3H), 2.37 (s, 3H), 2.91–2.99 (m, 1H), 2.97 (t, J=7 Hz, 2H), 3.13 (dd, J=8 Hz, 14 Hz, 1H), 4.10 (q, J=7 Hz, 2H), 4.21 (t, J=7 Hz, 2H), 4.36 (dd, J=7 Hz, 8 Hz, 1H), 6.80 (d, J=8 Hz, 2H), 7.09 (d, J=8 Hz, 2H), 7.38–7.42 (m, 3H), 7.94–7.98 (m, 2H).

EXAMPLE 4

3-[2-((5-Methyl-2-phenyl-4-oxazolyl)methyl)benzofuran-5-yl]-2-(propylthio)propanoate A. alpha-(5-Methyl-2-phenyl-4-oxazolyl)-5-nitro-2-benzofuranmethanol A solution of 4-bromoacetyl-5-methyl-2-phenyloxazole (Takeda U.S. Pat. No. 4,725,610) (53 g, 0.19 mol), 5-nitrosalicyladehyde (32 g, 0.19 mol) and diisopropylethylamine (66 ml, 0.38 mol) in dimethylformamide (250 ml) was heated to 91°–94° C. for 3 hours. The mixture was cooled, diluted with ethyl acetate (300 ml) and the solid was collected. This solid was washed with chloroform (2×100 ml) and dried (56 g, mp 233°–234° C.). It was then placed in tetrahydrofuran (600 ml) and methanol (300 ml) and the slurry was cooled to 0° C. Sodium borohydride (9.1 g, 0.24 mol) was added portion-wise over 1 hour and the cloudy solution was stirred at 0° C. for 2 hours. The bulk of the solvent was removed in vacuo and water (700 ml) was added. The mixture was acidified with 6N hydrochloric acid and stirred for 30 minutes. The yellow-tan solid was collected, washed with water and dried (57 g, mp 166°–167° C.).

B. 5-Amino-2-(5-methyl-2-phenyl-4-oxazolyl)-methylbenzofuran alpha-(5-Methyl-2-phenyl-4-oxazolyl)-5-nitro-2-benzofuranmethanol (57 g, 0.16 mol) was dissolved in trifluoroacetic acid (350 ml), while cooling to 0° C. Triethylsilane (64 ml, 0.40 mol) was added. The solution was stirred 1.5 hours at 0° C. and overnight at room temperature. The solution was concentrated to near-dryness and the residue dissolved in ethyl acetate (750 ml). This solution was washed with water. The precipitate formed during the wash was collected. The organic solution was washed with saturated sodium bicarbonate, during which more precipitate formed and was collected. The ethyl acetate phase of the filtrate was washed again with saturated sodium bicarbonate, then with brine, dried over sodium sulfate and concentrated. The residue was triturated with isopropyl ether and a solid was obtained. The combined solids obtained hereinabove (51 g, 0.15 mol) were placed in a Parr bottle together with platinum oxide (3 g) and ethyl acetate (1.5 l) and hydrogenated at 40 psi (2.81×10$^4$ Kg/m$^2$) for 1.25 hours. The catalyst was filtered through Celite, and after washing the filtering pad with more ethyl acetate, the solvent was removed in vacuo to give a yellow residue which was triturated with isopropyl ether (200 ml). The pale yellow solid was collected (37.1 g, mp 161.5°–162.5° C.).

C. alpha-Chloro-2-(5-methyl-2-phenyl-4-oxazolyl)-methyl-5-benzofuranpropanenitrile To a solution of acrylonitrile (11.2 ml, 0.17 mol) and tert-butyl nitrite (21.4 ml, 0.18 mmol) in acetonitrile (16 ml) was added cupric chloride (19.4 g, 0.14 mol), and 5-amino-2-(5-methyl-2-phenyl-4-oxazolyl)methylbenzofuran (37 g, 0.12 mol) portionwise over 40 minutes. The mixture was stirred for 30 minutes then poured into 20% hydrochloric acid (500 ml) and this solution was extracted with ethyl acetate (2×700 ml). The combined extracts were washed with 20% hydrochloric acid (2×250 ml), and brine (350 ml), dried over sodium sulfate and concentrated. The thick gum was extracted with boiling hexane (4×450 ml), the combined liquid phases were decanted, boiled down to ca. 1100 ml and cooled. The solid was collected (6.9 g). The mother liquor was concentrated and the residue was purified by flash-chromatography (hexanes/ethyl acetate, 4:1) to give a yellow solid which was combined with the material obtained from the hot hexane to give 16 g of the title compound as a yellow sticky solid.

D. Ethyl 3-[2-((5-Methyl-2-phenyl-4-oxazolyl)methyl)benzofuran-5-yl]-2-(propylthio)-propanoate Hydrogen chloride was bubbled into a slurry of 2-(5-methyl-2-phenyl-4-oxazolyl)methyl-alpha-chloro-5-benzofuranpropanenitrile (16.3 g, 43 mmol) in 95% ethanol (600 ml) at 0° C. for 30 minutes, after which the mixture was stirred for 3 days at room temperature. The solvent was removed in vacuo and the residue partitioned between saturated sodium bicarbonate (350 ml) and ethyl acetate (500 ml). The aqueous layer was extracted with ethyl acetate (250 ml), the organic phases were combined, washed with brine, dried over sodium sulfate and concentrated. The oily residue was extracted with boiling hexane (2×400 ml), the solution was boiled down to 400 ml and cooled. The precipitated solid was collected. The filtrate was boiled down to 250 ml and allowed to cool overnight and the solid was collected. The two solids were combined (11.5 g, mp 113°–115° C.).

To a solution of this solid (5 g, 12 mmol) in dimethylformamide (100 ml) was added propyl mercaptan (3.0 gml, 33 mmol), followed by potassium carbonate (4.6 g, 33 mmol). The slurry was stirred at room temperature overnight then poured into water (400 ml), acidified with 6N hydrochloric acid and extracted with ethyl acetate (2×300 ml). The combined extracts were washed with water (3×200 ml) and brine, dried over sodium sulfate and concentrated, leaving a yellow oil (4.3 g).

$^1$H NMR (CDCl$_3$, 300 MHz), delta 0.93 (t, J=7.5 Hz, 3H), 1.15 (t, J=7.0 Hz, 3H), 1.56 (m, 2H), 2.32 (s, 3H), 2.57 (m, 2H), 2.99 (dd, J=6.4 Hz, 13.9 Hz, 1H), 3.22 (dd, J=9.4 Hz, 13.6 Hz, 1H), 3.48 (dd, J=6.4 Hz, 9.1 Hz, 1H), 3.99 (s, 2H), 4.08 (m, 2H), 6.40 (d, J=1.1 Hz, 1H), 7.03 (dd, J=1.6 Hz, 8.6 Hz, 1H), 7.29 (s, 1H), 7.29 (d, J=7.8 Hz, 1H), 7.37–7.42 (m, 3H), 7.96–7.99 (m, 2H).

Using the corresponding mercaptans, the following compounds were prepared by the same procedure:

Ethyl 3-[2-((5-methyl-2-phenyl-4-oxazolyl)methyl)-benzofuran-5-yl]-2-(phenylmethylthio)propanoate (oil)

$^1$H NMR (CDCl$_3$, 300 MHz) delta 1.20 (t, J=7 Hz, 3H), 2.32 (s, 3H), 2.92 (dd, J=6 Hz, 14 Hz, 1H), 3.20

(dd, J=9 Hz, 14 Hz, 1H), 3.45 (dd, J=6 Hz, 9 Hz, 1H), 3.75 (d, J=13 Hz, 1H), 3.80 (d, J=13 Hz, 1H), 4.0 (s, 2H), 4.05 (m, 2H), 6.38 (s, 1H), 6.90 (dd, J=2 Hz, 8 Hz), 7.10–7.30 (m, 7H), 7.35–7.45 (m, 3H), 7.92–8.00 (m, 2H).I

Ethyl 2-ethylthio-3-[2-((methyl-2-phenyl-4-oxazolyl)-methyl)benzofuran-5-yl]propanoate (oil)

$^1$H NMR (CDCl$_3$, 300 MHz) delta 1.15 (t, J=7.4 Hz, 3H), 1.20 (t, J=7.7 Hz, 3H), 2.32 (s, 3H), 2.61 (dq, J=1.4 Hz, 7.8 Hz, 2H), 3.07 (dd, J=6.3 Hz, 13.8 Hz, 1H), 3.23 (dd, J=9.6 Hz, 13.9 Hz, 1H), 3.50 (dd, J=6.3 Hz, 9.1 Hz, 1H), 3.99 (s, 2H), 4.08 (m, 2H), 6.40 (s, 1H), 7.03 (dd, J=1.65 Hz, 8.6 Hz, 1H), 7.29 (s, 1H), 7.29 (d, J=8.3 Hz, 1H), 7.37–7.42 (m, 3H), 7.42–7.99 (m, 2H).

Ethyl 3-[2-((5-methyl-2-phenyl-4-oxazolyl)methyl-benzofuran-5-yl]-2-(phenylthio)propanoate (oil)

$^1$H NMR (CDCl$_3$, 300 MHz) delta 1.04 (t, J=7 Hz, 3H), 2.32 (s, 3H), 3.08 (dd, J=6 Hz, 14 Hz, 1H), 3.22 (dd, J=9 Hz, 14 Hz, 1H), 3.88 (dd, J=6 Hz, 9 Hz, 1H), 3.95 (m, 2H), 4.00 (s, 3H), 6.38 (s, 1H), 7.00 (d, J=8 Hz, 1H), 7.21–7.30 (m, 6H), 7.35–7.45 (m, 4H), 7.92–7.99 (m, 2H).

Ethyl 3-[2-((5-methyl-2-phenyl-4-oxazolyl)methyl)-benzofuran-5-yl]-2-(octylthio)propanoate (oil)

$^1$H NMR (CDCl$_3$, 300 MHz) delta 0.85 (t, J=6.5 Hz, 3H), 1.18 (t, J=7.0 Hz, 3H), 1.22–1.35 (m, 10H), 1.47–1.58 (m, 2H), 2.33 (s, 3H), 2.58 (m, 2H), 2.99 (dd, J=6.3 Hz, 13.8 Hz, 1H), 3.22 (dd, J=9.2 Hz, 13.8 Hz, 1H), 3.48 (dd, J=6.3 Hz, 9.2 Hz, 1H), 3.99 (s, 2H), 4.08 (m, 2H), 6.40 (s, 1H), 7.03 (dd, J=1.8 Hz, 8.5 Hz, 1H), 7.28 (s, 1H), 7.29 (d, J=7.9 Hz, 1H), 7.37–7.42 (m, 3H), 7.95–7.99 (m, 2H).

EXAMPLE 5

3-[2-((5-Methyl-2-phenyl-4-oxazolyl)methyl)benzofuran-5-yl-2-(propylthio]propanoic Acid To a solution of title product of Example 4 (3.8 g, 8.2 mmol) in methanol (100 ml) was added 1N sodium hydroxide (100 ml). The mixture was heated to reflux for 2 hours, cooled, poured onto ice (300 ml) and acidified with 6N hydrochloric acid, then extracted with ethyl acetate (500 ml), during which some precipitated solid was collected. The aqueous phase was extracted again with ethyl acetate (200 ml), the combined extracts were washed with water (300 ml) and brine (300 ml), dried over sodium sulfate and concentrated, leaving a yellow-orange solid. The solids were combined and recrystallized from ethyl acetate (150 ml) to give the title compound as an off-white solid (2.5 g, mp 169°–170° C.).

The following compounds were prepared by the same route from the corresponding ethyl esters:

3-[2-((5-Methyl-2-phenyl-4-oxazolyl)methyl)benzofuran-5-yl]-2-propanoic acid (mp 153°–154° C.)

2-Ethylthio-3-[2-((5-methyl-2-phenyl-4-oxazolyl)-methyl)benzofuran-5-yl]propanoic acid (mp 144°–145° C.)

3-[2-((5-Methyl-2-phenyl-4-oxazolyl)methyl)benzofuran-5-yl]-2-(phenylthio)propanoic acid (mp 160°–161° C.)

3-[2-((5-Methyl-2-phenyl-4-oxazolyl)methyl)benzofuran-5-yl]-2-(octylthio)propanoic acid (mp 94°–96° C.)

EXAMPLE 6

3-[2-((5-Methyl-2-phenyl-4-oxazolyl)methylbenzofuran-5-yl]-2-(methylthio)propanoic Acid 5-Amino-2-[(5-methyl-2-phenyl-4-oxazolyl)methyl]-benzofuran was converted into the title compound according to the procedure of Example 2. Mp 178°–179° C.

3-[2-[5-Methyl-2-(3-methylphenyl)-4-oxazolyl]methyl-benzofuran-5-yl]-2-(methylthio)propanoic acid was prepared by the same procedure using the corresponding starting material. Mp 125°–127° C.

EXAMPLE 7

Ethyl 2-(Acetylthio)-3-[2-((5-methyl-2-phenyl-4-oxazolyl)methyl)benzofuran-5-yl]propanoate was prepared from ethyl alpha-bromo-2-(5-methyl-2-phenyl-4-oxazolyl)methyl-5-benzofuranpropanoic acid according to the procedure of Example 3 and obtained as an oil.

$^1$H NMR (CDCl$_3$, 300 MHz) delta 1.10 (t, J=7 Hz, 3H), 2.29 (s, 3H), 2.34 (s, 3H), 3.04 (dd, J=7 Hz, 14 Hz, 1H), 3.25 (dd, J=8 Hz, 14 Hz, 1H), 3.99 (s, 2H), 4.07 (q, J=7 Hz, 2H), 4.38 (dd, J=7 Hz, 8 Hz, 1H), 6.40 (s, 1H), 7.03 (dd, J=2 Hz, 8 Hz, 1H), 7.28 (s, 1H), 7.36–7.42 (m, 3H), 7.00 (4–7.98 (m, 2H).

Ethyl 2-((acetylthio)-3-[2-[(5-methyl-2-(3-methylphenyl)-4-oxazolyl)methyl]benzofuran-5-yl]-propanoate was prepared according to the same procedure and obtained as an oil.

$^1$H NMR (CDCl$_3$, 300 MHz) delta 1.10 (t, J=7 Hz, 3H), 2.30 (s, 3H), 2.35 (s, 3H), 2.40 (s, 3H), 3.05 (dd, J=7 Hz, 14 Hz, 1H), 3.27 (dd, J=8 Hz, 14 Hz, 1H)), 4.00 (s, 2H), 4.07 (q, J=7 Hz, 2H), 4.39 (dd, J=7 Hz, 8 Hz, 1H), 6.40 (s, 1H), 7.04 (dd, J=2 Hz, 8 Hz, 1H), 7.18 (d, J=8 Hz, 1H), 7.26–7.30 (m, 3H), 7.75 (d, J=8 Hz, 1H), 7.81 (s, 1H).

EXAMPLE 8

Ethyl 3-[2-((5-methyl-2-phenyl-4-oxazolyl)methyl)benzofuran-5-yl]-2-(propylsulfinyl)-propanoate To a solution of title product of Example 4 (0.39 g, 0.85 mmol) in tetrahydrofuran (75 ml) was added at 0° C., 80% m-chloroperoxybenzoic acid (0.18 g, 0.85 mmol). After 10 minutes, ethyl vinyl ether (0.5 ml) was added and the solution was diluted with ethyl acetate, washed with water (3×) and brine, dried over magnesium sulfate and concentrated. Flash-chromatography (hexanes/ethyl acetate, 2:1) gave the expected product as an oil (0.35 g).

$^1$H NMR (CDCl$_3$, 300 MHz) delta 1.05 (t, J=7 Hz, 3/2H), 1.09 (t, J=7 Hz, 3/2H), 1.12 (t, J=7 Hz, 3/2H), 1.19 (t, J=7.1 Hz, 3/2H), 1.73–1.94 (m, 2H), 2.34 (s, 3H), 2.56–2.88 (m, 2H), 3.27–3.46 (m, 2H), 3.71–3.78 (m, 1H), 4.01 (s, 2H), 4.05–4.26 (m, 2H), 6.41 (d, J=0.7 Hz, ½H), 6.42 (d, J=1.0 Hz, ½H), 7.04 (dd, J=1.7 Hz, 6.9 Hz, ½H), 7.07 (dd, J=1.8 Hz, 6.7 Hz, ½H), 7.30–7.33 (m, 2H), 7.36–7.43 (m, 3H), 7.92–8.03 (m, 2H).

EXAMPLE 9

3-[2-((5-Methyl-2-phenyl-4-oxazolyl)methyl)benzofuran-5-yl]-2-(methylsulfonyl)propionic acid To a solution of title product of Example 5 (0.30 g, 0.74 mmol) in tetrahydrofuran (75 ml) was added 80% m-chloroperoxybenzoic acid (0.16 g, 0.74 mmol) at 0° C. After 10 minutes, ethyl vinyl ether (0.5 ml) was added, the solution was diluted with ethyl acetate, washed with water (3×) and brine, dried over magnesium sulfate and concentrated. The product was isolated by flash-chromatography (hexane/ethyl acetate, 1:1) as a yellow solid (0.11 g, mp 220°–203° C.).

EXAMPLE 10

3-[2-((5-Methyl-2-phenyl-4-oxazolyl)methylbenzofuran-5-yl]-2-(propylsulfinyl)propanoic Acid A solution of the title product of Example 8 (0.20 g, 0.42 mmol) in methanol (5 ml) and 1N sodium hydroxide (5 ml) was stirred at room temperature for 48 hours. It was then poured into water, acidified with concentrated hydrochloric acid and extracted with ethyl acetate (3×). The combined extracts were washed with water and brine, dried over sodium sulfate and concentrated to an oil. The product was purified by flash-chromatography (ethyl acetate/hexane, 10:1) and obtained as an oily solid (43 mg).

$^1$H NMR (CDCl$_3$, 300 MHz, 62° C.) delta 0.88 (t, J=7 Hz, 3/2H), 0.97 (t, J=7 Hz, 3/2H), 1.60 (m, 1H), 1.75 (m, 1H), 2.34 (s, 3/2H), 2.36 (s, 3/2H), 2.55–2.70 (m, 1H), 2.80 (m, ½H), 2.91 (m, ½H), 3.05 (m, ½H), 3.35 (m, 1H), 3.42–3.51 (m, 1.5H), 3.97 (s, 2/2H), 3.99 (s, 2/2H), 6.34 (s, ½H), 6.38 (s, ½H), 7.06 (d, J=7 Hz, 1H), 7.20–7.27 (m, 1H), 7.31–7.37 (m, 4H), 7.92–7.95 (m, 2H).

EXAMPLE 11

3-[2-((5-Methyl-2-phenyl-4-oxazolyl)methyl)benzofuran-5-yl]-2-(methylthio)-N-(phenylsulfonyl)propanamide A mixture of the title product of Example 6 (0.15 g, 0.37 mmol) and thionyl chloride (0.10 ml, 1.4 mmol) was heated on a steam bath for 20 minutes. The mixture was cooled, diluted with benzene and concentrated. A mixture of benzenesulfonamide (0.12 g, 0.74 mmol) and 60% sodium hydride (32 mg, 0.81 mmol) in tetrahydrofuran (5 ml) was heated at reflux for 30 minutes, cooled to 0° C. and treated with a solution of this acid chloride in tetrahydrofuran (5 ml). The mixture was heated for 3 hours at reflux and overnight at room temperature. It was then diluted with ethyl acetate, washed with 1N hydrochloric acid, water (2×) and brine, dried over magnesium sulfate and concentrated. The product was purified by flash-chromatography (3% methanol in dichloromethane) and obtained as an oil.

$^1$H NMR (CDCl$_3$, 300 MHz) delta 1.90 (s, 3H), 2.36 (s, 3H), 2.92 (dd, J=8 Hz, 14 Hz, 1H), 3.14 (dd, J=8 Hz, 14 Hz, 1H), 3.38 (t, J=8 Hz, 1H), 3.99 (s, 3H), 6.33 (s, 1H), 6.80 (dd, J=2 Hz, 8 Hz, 1H), 7.09 (d, J=2 Hz, 1H), 7.17 (dd, J=2 Hz, 8 Hz, 1H), 7.38–7.60 (m, 6H), 7.94–7.98 (m, 4H), 9.00 (br s, 1H).

By the same method the following compounds were prepared: 3-[2-((5-Methyl-2-phenyl-4-oxazolyl)methyl)-benzofuran-5-yl]-2-(methylthio)-N-(phenylcarbonyl)-propanamide (mp 62° C.).

3-[2-((5-Methyl-2-phenyl-4-oxazolyl)methyl)benzofuran-5-yl]-2-(methylthio)-N-(4-chlorophenylsulfonyl)-propanamide (mp 94°-95° C.). (mp 94°-95° C.).

3-[2-((5-Methyl-2-phenyl-4-oxazolyl)methyl)benzofuran-5-yl]-2-(methylthio)-N-(4-fluorophenylsulfonyl)-propanamide (mp 60°-62° C.).

3-[2-((5-Methyl-2-phenyl-4-oxazolyl)methyl)benzofuran-5-yl]-2-(methylthio)-N-(methanesulfonyl)propanamide (mp 63°-64° C.).

3-[2-((5-Methyl-2-phenyl-4-oxazolyl)methyl)benzofuran-5-yl]-2-(methylthio)-N-[(E)-2-phenylethenylsulfonyl]propanamide (oil).

$^1$H NMR (CDCl$_3$, 300 MHz) delta 2.05 (s, 3H), 2.34 (s, 3H), 3.02 (dd, J=8 Hz, 14 Hz, 1H), 3.25 (dd, J=8 Hz, 14 Hz, 1H), 3.48 (t, J=8 Hz, 1H), 3.98 (s, 2H), 6.30 (s, 1H), 6.95 (d, J=14 Hz, 1H), 6.96 (dd, J=2 Hz, 8 Hz, 1H), 7.22 (d, J=2 Hz, 1H), 7.35–7.48 (m, 9H), 7.69 (d, J=14 Hz, 1H), 7.95–8.0 (m, 2H), 9.20 (br s, 1H).

3-[2-(5-Methyl-2-phenyl-4-oxazolyl)methyl)benzofuran-5-yl]-2-(methylthio)-N-(2-naphthylsulfonyl)-propanamide (mp 163°-166° C.).

3-[2-((5-Methyl-2-phenyl-4-oxazolyl)methyl)benzofuran-5-yl]-2-(methylthio)-N-(N,N-diethylaminosulfonyl)propanamide (oil).

$^1$H NMR (CDCl$_3$, 300 MHz) delta 1.12 (t, J=7 Hz, 6H), 2.08 (s, 3H), 2.36 (s, 3H), 2.96 (dd, J=8 Hz, 14 Hz, 1H), 3.30 (q, J=7 Hz, 4H), 3.40 (t, J=8 Hz, 1H), 4.00 (s, 2H), 6.41 (s, 1H), 7.01 (dd, J=2 Hz, 8 Hz, 1H), 7.26 (dd, J=2 Hz, 1H), 7.30 (d, J=8 Hz, 1H), 7.38–7.42 (m, 3H), 7.92–7.96 (m, 2H), 8.72 (s, 1H).

EXAMPLE 12

Optical Resolution of
3-[2-((5-methyl-2-phenyl-4-oxazolyl)methyl)benzofuran-5-yl]-2-(propylthio)-propanoic Acid To a slurry of title product of Example 5 (1.6 g, 3.8 mmol) in benzene (35 ml) was added oxalyl chloride (1.8 ml, 21 mmol). Gas was evolved and the slurry turned into a clear yellow solution within 10 minutes. After two hours the solvent was removed, the residue was dissolved in dioxane (25 ml) and added dropwise to, a solution of (S)-(+)-2-phenylglycinol (0.52 g, 3.8 mmol) and triethylamine (0.53 ml) in dioxane (10 ml). After 2 hours, the solvent was removed, water was added to the residue and the mixture was acidified with 6N hydrochloric acid. The solid was collected, dried and recrystallized from ethyl acetate/hexanes then from ethyl acetate to give the less polar isomer (on silica thin-layer chromatography, hexane/ethyl acetate, 1:2) as a pale yellow solid (0.41 g). The combined mother liquors were concentrated and the products separated by flash-chromatography (hexane/ethyl acetate, 1:1). More of the less polar isomer was thus obtained (0.14 g) as well as the more polar isomer (0.39 g).

The less polar amide (0.54 g, 0.97 mmol) and p-toluenesulfonic acid (2.8 g, 15 mmol) were placed in water (20 ml) and isopropanol (20 ml) and heated to reflux for three days. The solution was cooled, diluted with water (75 ml) and extracted with ethyl acetate (2×75 ml). The combined extracts were washed with water (2×75 ml) and brine (75 ml), dried over sodium sulfate and concentrated. The product was purified by flash chromatography (hexanes/ethyl acetate/acetic acid, 16:4:1), then recrystallized from ethyl acetate (15 ml)/hexane (5 ml). The mother liquor was concentrated to give a white solid (83 mg, [alpha]$_D$= +8.8°, c=1.08, CDCl$_3$). This material was subsequently found to be greater than 95% optically pure by conversion back to the amide under neutral conditions (EEDQ) and its NMR spectrum was identical to the one of the racemic material.

In the same manner the more polar amide (0.39 g, 0.71 mmol) was converted into the levorotatory acid (81 mg, [alpha]$_D$= −9.4°, c=1.06, CDCl$_3$).

EXAMPLE 13

2-Methoxy-3-[4-[2-(5-methyl-2-phenyl-4-oxazolyl)ethoxy]phenyl]propanoic Acid

A. 4-[2-(5-Methyl-2-phenyl-4-oxazolyl)ethoxy]benzeneacetaldehyde

To a slurry of methoxymethyltriphenylphosphonium chloride (11 g, 32 mmol) in tetrahydrofuran (120 ml), cooled to 0° C., was added dropwise a 2.5M solution of n-butyllithium in hexanes (9.8 ml, 25 mmol). The red solution was stirred at 0° C. for 30 minutes then a solution of 4-[2-(5-methyl-2-phenyl-4-oxazolyl)ethoxy]-benzaldehyde (Takeda U.S. Pat. No. 4,725,610) (5.0 g, 16 mmol) in tetrahydrofuran (70 ml) was added dropwise. The mixture was allowed to warm to room temperature and stirred overnight. It was then diluted with water and extracted with ethyl acetate (3×). The combined extracts were washed with water (2×) and brine, dried over sodium sulfate and concentrated. The product, a mixture of E and Z 4-[2-[4-(2-methoxyethenyl)phenoxy]-ethyl]-5-methyl-2-phenyloxazole, was isolated by flash-chromatography (hexanes/ethyl acetate, 2:1) as a yellow solid (2.6 g).

This solid (2.0 g, 6.0 mmol) was dissolved in tetrahydrofuran (100 ml) and 35% perchloric acid (10 ml) was added. The solution was heated to reflux for 1 hour then stirred overnight at room temperature, then diluted with water and extracted with ethyl acetate (2×). The combined extracts were washed with water and brine, dried over sodium sulfate and concentrated. The residue was purified by flash-chromatography (hexane/ethyl acetate, 4:1) and a yellow solid (0.51 g) was obtained.

B. Ethyl alpha-hydroxy-4-[2-(5-methyl-2-phenyl-4-oxazolyl)ethoxy]benzenepropanoate To a solution of 4-[2-(5-methyl-2-phenyl-4-oxazolyl)ethoxy]benzeneacetaldehyde (0.51 g, 1.6 mmol) and trimethylsylyl cyanide (0.21 ml, 1.6 mmol) in deuterochloroform (1 ml) was added zinc iodide (1 crystal). The solution was stirred overnight at room temperature, then concentrated to yield the product, 4-[2-(5-methyl-2-phenyl-4-oxazolyl)ethoxy]-alpha(trimethylsilyloxy)benzenepropanenitrile, as an oil.

This oil was dissolved in hydrogen chloride (50 ml), the solution was cooled to 0° C., saturated with hydrogen chloride, and stirred overnight at room temperature, then saturated with hydrogen chloride again and stirred another 24 hours at room temperature. The mixture was poured into water, ethyl acetate was added, then 1N sodium hydroxide so as to get the product in solution. The organic layer was separated, washed with water and brine, dried over sodium sulfate and concentrated to a brown oil which was purified by flash-chromatography (hexanes/ethyl acetate, 3:2). The pure product was obtained as an oil (0.19 g).

C. 2-Methoxy-4-3-[2-(5-methyl-2-phenyl-4-oxazolyl)ethoxy)phenylpropanoic acid

A 60% sodium hydride dispersion (40 mg) was washed with hexane and suspended in tetrahydrofuran (10 ml). A solution of ethyl alpha-hydroxy alpha-hydroxy-4-[2-(5-methyl-2-phenyl-4-oxazolyl)ethoxy]-benzenepropanoate (0.19 g, 0.48 mmol) in tetrahydrofuran (2 ml) was added and after 10 minutes methyl iodide (0.3 ml, 4.8 mmol) was added. The mixture was stirred at room temperature overnight, then diluted with water, acidified with 2N hydrochloric acid and extracted with ethyl acetate (2×). The combined extracts were washed with water and brine, dried over sodium sulfate and concentrated. The product was purified by flash-chromatography (hexanes/ethyl acetate/acetic acid, 10:10:1) and obtained as a yellow sticky solid.

$^1$H NMR (CDCl$_3$, 300 MHz) delta 2.36 (s, 3H), 2.96 (m, 3H), 3.05 (dd, J=6 Hz, 14 Hz, 1H), 3.37 (s, 3H), 3.93 (dd, J=6 Hz, 9 Hz, 1 H), 4.17 (t, J=9 Hz, 2H), 6.79 (d, J=8 Hz, 1H), 7.10 (d, J=8 Hz, 1H), 7.36–7.40 (m, 3H), 7.92–7.96 (m, 2H).

EXAMPLE 14

2-Methoxy-3-[2-((5-methyl-2-phenyl-4-oxazolyl)methyl)benzofuran-5-yl]propanoic Acid A. 4-Benzoylamino-1-hexyn-5-one Acetic anhydride (150 ml) was added to a solution of 2-benzoylamino-4-pentynoic acid (J. Org. Chem. 1983, 48, 3318) (73 g, 0.34 mol) in pyridine (200 ml) and the solution was heated to 90° C. for 1 hour, then allowed to cool to 60° C. and water (150 ml) was added. The mixture was heated to 85°–90° C. for 20 minutes, then cooled, diluted with water (300 ml) and extracted with chloroform (2×400 ml). The combined extracts were washed with water, 1N hydrochloric acid (3×500 ml), sodium bicarbonate and brine, and dried over magnesium sulfate. The chloroform solution was decolorized with charcoal, filtered and concentrated. The residue was recrystallized from butyl chloride to yield a tan solid (51 g, mp 101°–103° C.).

B. 5-Methyl-2-phenyl-4-(2-propynyl)oxazole

A solution of 4-benzoylamino-1-hexyn-5-one (30 g, 0.14 mol) in trifluoroacetic anhydride (100 ml) and trifluoroacetic acid (200 ml) was heated to 35°–40° C. for 6 hours. The solution was concentrated and the residue taken up in ethyl acetate (400 ml). To this solution was added saturated sodium bicarbonate solution (400 ml) followed by solid sodium bicarbonate until the water layer became neutral. The layers were separated, the organic layer was washed with brine, dried over magnesium sulfate and concentrated to give a brown oil (28 g) which was used as such.

C. 2-(5-Methyl-2-phenyl-4-oxazolyl)methyl-5-benzofurancarboxaldehyde

To a slurry of cuprous oxide (12 g, 84 mmol) in pyridine (150 ml) were added a solution of 5-methyl-2-phenyl-4-(2-propynyl)oxazole in pyridine (150 ml) followed by a solution of 4-hydroxy-3-iodobenzaldehyde (35 g, 0.14 mol) in pyridine (100 ml). Bis(triphenylphosphine)palladium (II) chloride (0.50 g, 0.7 mmol) was then added as a solid and the mixture was heated to reflux overnight. The mixture was cooled and concentrated. The residue was taken up in ethyl acetate (250 ml+3×50 ml). The ethyl acetate solution was concentrated and the residue was extracted with hot cyclohexane. The hot solution was filtered and cooled and the solid was collected (29 g).

D. 5-(2-Methoxyethenyl)-2-[((5-methyl-2-phenyl-4-oxazolyl)methyl]benzofuran

To a slurry of methoxymethylphosphonium chloride (34 g, 0.10 mol) and diisopropylamine (9.9 ml, 75 mmol) in tetrahydrofuran (500 ml) was added a 2.5M n-butyllithium solution in hexanes (30 ml, 75 mmol) at −10° C. After 1 hour at 10° C. a solution of 2-(5-methyl-2-phenyl-4-oxazolyl)methyl-5-benzofurancarboxaldehyde (16 g, 50 mmol) in tetrahydrofuran (200 ml) was added. The mixture was allowed to warm to room temperature over 2 hours, then poured into water (600 ml) and extracted with ether (3×). The combined extracts were washed with brine, dried over magnesium sulfate and concentrated. The product was isolated by flash-chromatography (hexanes/ethyl acetate, 4:1) as a solid (14 g).

E. 5-(2,2-Dimethoxyethyl)-2-[(5-methyl-2-phenyl-4-oxazolyl)methyl]benzofuran

A solution of 5-(2-methoxyethenyl)-2-(5-methyl-2-phenyl-4-oxazolyl)methylbenzofuran (0.69 g, 2.0 mmol) and p-toluenesulfonic acid monohydrate (40 mg, 0.21 mmol) in methanol (30 ml) was heated to reflux overnight. The solvent was removed, the residue was taken up in ethyl acetate, the solution was washed with 5% sodium bicarbonate and brine, dried over magnesium sulfate and concentrated to an oil which slowly solidified on standing (0.75 g).

F. 2-Methoxy-3-[2-((5-methyl-2-phenyl-4-oxazolyl)methyl)benzofuran-5-yl]propanenitrile To a solution of 5-(2,2-dimethoxyethyl)-2-[(5-methyl-2-phenyl-4-oxazolyl)methyl]benzofuran (0.75 g, 2.0 mmol) in dichloromethane (15 ml) were added trimethylsilyl cyanide (0.80 ml, 6.0 mmol) and boron trifluoride etherate (50 µl, 0.5 mmol). After 1 hour the solution was diluted with dichloromethane, washed with 5% sodium bicarbonate, water and brine, dried over magnesium sulfate and concentrated. The product was purified by flash-chromatography (hexanes/ethyl acetate, 2:1) and isolated as a solid (0.64 g, mp 107°-109° C.).

G. 2-Methoxy-3-[2-((5-methyl-2-phenyl-4-oxazolyl)methyl)benzofuran-5-yl]propanoic acid A mixture of 2-methoxy-3-[2-((5-methyl-2-phenyl-4-oxazolyl)methyl)benzofuran-5-yl]propanenitrile (0.64 g, 1.7 mmol), ethanol (30 ml) and 6N sodium hydroxide (10 ml) was heated to reflux for 3 hours. Water (30 ml) was added and the solution was acidified with concentrated hydrochloric acid (6 ml), then extracted with ethyl acetate (2×). The combined organic layers were washed with brine, dried over magnesium sulfate and concentrated. The product was recrystallized from ethyl acetate/hexanes and obtained as a white solid (0.47 g, mp 159°-160° C.).

Using the corresponding alcohols, the following compounds were prepared by the same procedure:

2-Ethoxy-3-[2-((5-methyl-2-phenyl-4-oxazolyl)methyl)benzofuran-5-yl]propanoic acid (mp 164°-165.5° C.)

3-[2-((5-Methyl-2-phenyl-4-oxazolyl)methyl)benzofuran-5-yl]-2-propoxypropanoic acid (mp 139.5°-140.5° C.)

3-[2-(5-Methyl-2-phenyl-4-oxazolyl)methyl)benzofuran-5-yl]-2-(2-propenyloxy)propanoic acid (mp 154°-155.5° C.)

3-[2-((5-Methyl-2-phenyl-4-oxazolyl)methyl)benzofuran-5-yl]-2-(benzyloxy)propanoic acid (mp 123°-126° C.)

2-(3-Hydroxypropoxy)-2-[2-((5-methyl-2-phenyl-4-oxazolyl)methyl)benzofuran-5-yl]propanoic acid (mp 125°-127° C.) 3-[2-(5-Methyl-2-phenyl-4-oxazolyl)methyl)benzofuran-5-yl]-2-(2-propynyloxy)propanoic acid (mp 148°-150° C.)

From (2H)-3,4-dihydro-2-[(4-(benzyloxybenzyl-6-benzopyrancarboxaldehyde (U.S. Pat. No. 4,798,835), sodium (2H)-3,4-dihydro-alpha-ethoxy-2-(4-benzyloxybenzyl)-6-benzopyranpropanoate was prepared by the same sequence. Mp 61°-64° C.

EXAMPLE 15

2-Methoxy-3-[2-((5-methyl-2-phenyl-4-oxazolyl)methyl)benzofuran-5-yl]propanamide A solution of the Step F intermediate, Example 14 (0.24 g, 0.64 mmol) in ethanol (20 ml) was saturated with hydrogen chloride and stirred at room temperature for three days. The solvent was removed, water was added followed by saturated sodium bicarbonate to bring the pH to neutral. This mixture was extracted with ethyl acetate (2×), the combined extracts were washed with brine and dried over magnesium sulfate overnight. The product was isolated by flash-chromatography (hexanes/ethyl acetate, 1:1) as a white solid (58 mg, mp 164°-167° C.).

2-Ethoxy-3-[2-((methyl-2-phenyl-4-oxazolyl)methyl)benzofuran-5-yl]propanamide was obtained by the same method. Mp 165°-168° C.

EXAMPLE 16

(E) and (Z)-3-[2-((5-Methyl-2-phenyl-4-oxazolyl)methyl)benzofuran-5-yl]-2-methoxy-2-propenamide A (E) and (Z)-3-[2-((5-Methyl-2-phenyl-4-oxazolyl)methylbenzofuran-5-yl]-2-methoxy-2-propenenitrile To a slurry of 60% sodium hydride (88 mg, 2.2 mmol) in dimethylformamide (15 ml) was added at 45° C. methoxyacetonitrile (0.21 g, 2.0 mmol). This solution was allowed to cool and after 30 minutes was slowly added to a warm (50° C.) solution of 2-(5-methyl-2-phenyl-4-oxazolyl)methyl-5-benzofurancarboxaldehyde (Example 14) (0.63 g, 2.0 mmol) in dimethylformamide (10 ml). The mixture was heated to 75°-80° C. for 1 hour then cooled and poured into a water/ethyl acetate mixture. The layers were separated, the aqueous layer was extracted with ethyl acetate, the combined organic phases were washed with water (3×), dried over magnesium sulfate and concentrated. Flash-chromatography (hexanes/ethyl acetate, 2.5:1) afforded the two geometrical isomers of the product, the less polar isomer (assigned as Z) as a solid (0.10 g), and the more polar isomer (E) as an oil (0.15 g).

B. (Z)-3-[2-(5-methyl-2-phenyl-4-oxazolyl)methyl-5-benzofuranyl]-2-methoxy-2-propenamide A solution of (Z)-3-[2-(5-methyl-2-phenyl-4-oxazolyl)methyl-5-benzofuranyl]-2-methoxy-2-propenenitrile (0.10 g, 0.27 mmol) in methanol (10 ml) and sodium hydroxide (2 ml) was heated to reflux for 3 hours then cooled, acidified with 6N hydrochloric acid and extracted with ethyl acetate. The combined extracts were washed with brine, dried over magnesium sulfate and concentrated. The product was purified by flash-chromatography (ethyl acetate/methanol/acetic acid, 75:1:1) and obtained as a solid (31 mg, mp 166°-169° C.).

The (E) isomer was subjected to the same hydrolysis conditions, and the product isolated as a solid (26 mg, mp 160°-164° C.).

EXAMPLE 17

(E)-3-[2-(5-Methyl-2-phenyl-4-oxazolyl)-methyl-5-benzofuranyl]-2-phenoxy-2-propenamide

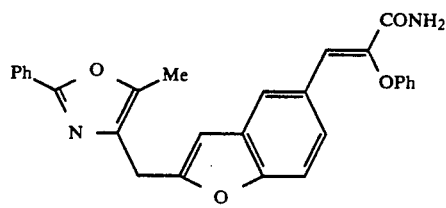

A. (E)-3-[2-(5-Methyl-2-phenyl-4-oxazolyl)methyl-5-benzofuranyl]-2-phenoxy-2-propenenitrile To a slurry of 60% sodium hydride (0.10 g, 2.5 mmol) in dimethylformamide (15 ml) was added at 60° C. phenoxyacetonitrile (0.21 g, 3.0 mmol). This solution was kept at 60° C. for 40 minutes, cooled to room temperature and was slowly added to a warm (80° C.) solution of 2-(5-methyl-2-phenyl-4-oxazolyl)methyl-5-benzofurancarboxaldehyde (0.40 g, 2.5 mmol) in dimethylformamide (20 ml). The mixture was heated to 75°-80° C. for 15 minutes, then cooled and poured into a solution of water (50 ml) and 1N HCl (2.5 ml). The mixture was extracted with ethyl acetate (2×). The combined organic phases were washed with water (3×) and brine, dried over magnesium sulfate and concentrated. Flash-chromatography (hexanes/ethyl acetate/triethylamine, 50:50:1) afforded the product as an oil (0.19 g).

B. (E)-3-[2-(5-Methyl-2-phenyl-4-oxazolyl)methyl)-5-benzofuranyl]-2-phenoxy-2-propenamide A solution of (E)-3-[2-(5-methyl-2-phenyl-4-oxazolyl)methyl-5-benzofuranyl]-2-phenoxy-2-propenenitrile (0.19 g, 0.44 mmol) in ethanol (10 ml) and sodium hydroxide (2 ml) was heated to reflux for 24 hours, then cooled, poured into a mixture of water (50 ml) and ethyl acetate and acidified with 6N hydrochloric acid. The layers were separated, the aqueous layer was extracted with ethyl acetate and the combined organic phases were washed with brine, dried over magnesium sulfate and concentrated. The product was purified by flash chromatography (hexanes/ethyl acetate/acetic acid, 48:8:1) followed by recrystallization from ethyl acetate/hexanes (30 mg, mp 171°-172.5° C.).

EXAMPLE 18

Sodium 2-benzyloxy-3-[2-(4-benzyloxybenzyl)-3,4-dihydro-2H-benzopyran-6-yl]propanoate

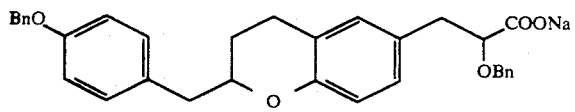

A. 2-(4-Benzyloxybenzyl)-3,4-dihydro-6-(2-methoxyethenyl)-2H-benzopyran

To a slurry of methoxymethylphosphonium chloride (12.5 g, 37 mmol) and diisopropylamine (9.9 ml, 27.5 mmol) in tetrahydrofuran (40 ml) was added a 2.5M n-butyllithium solution in hexanes (5.5 ml, 27.5 mmol) at −10° C. After 1 hour at −10° C. a slurry of 2-(4-benzyloxy)benzyl-3,4-dihydro-6-formyl-2H-benzopyran (U.S. Pat. No. 4,798,835) (4.9 g, 18 mmol) in tetrahydrofuran (100 ml) was added. The mixture was allowed to warm to room temperature over 2 hours, then was poured into water (200 ml) and extracted with ethyl acetate (3×). The combined extracts were washed with brine, dried over magnesium sulfate and concentrated. The product was isolated by flash-chromatography (hexanes/ethyl acetate, (4:1) as an oil (2.1 g).

B. 2-(4-Benzyloxybenzyl)-6-[2,2-bis(benzyloxy)ethyl]-3,4-dihydro-2H-benzopyran

A solution of 2-[(4-benzyloxy)benzyl]-3,4-dihydro-6-(2-methoxyethenyl)-2H-benzopyran (0.29 g, 0.75 mmol) and benzyl alcohol (1.0 ml, 9.7 mmol) containing Amberlyst 15 ® ion-exchange resin (100 mg) was heated to reflux overnight. The resin was filtered and washed with chloroform, the chloroform and the bulk of the benzyl alcohol were removed in vacuo and the residue was purified by flash-chromatography (hexanes/ethyl acetate, 4:1) to give the pure product as an oil (0.40 g).

C. 2-Benzyloxy-3-[2-(4-benzyloxybenzyl)-3,4-dihydro-2H-benzopyran-6-yl]propanenitrile To a mixture of 2-[(4-benzyloxy)benzyl]-6-[2,2-bis(-benzyloxy)ethyl]-3,4-dihydro-2H-benzopyran (0.40 g, 0.70 mmol) and trimethylsilyl cyanide (2 ml) was added boron trifluoride etherate (2.0 ml, 0.2 mmol). After 1 hour the reaction was quenched with saturated sodium bicarbonate and the solution was extracted with ethyl acetate (2×). The combined extracts were washed with brine, dried over magnesium sulfate and concentrated. The product was purified by flash-chromatography (hexanes/ethyl acetate, 2:1) and isolated as an oily solid (0.23 g).

D. Sodium 2-Benzyloxy-3-[-2-(4-benzyloxybenzyl)-3,4-dihydro-2H-benzopyran-6-yl]propanoate A mixture of 2-benzyloxy-3-[2-(4-benzyloxybenzyl)-3,4-dihydro-2H-benzopyran-6-yl]propanenitrile (0.23 g, 0.47 mmol), ethanol (10 ml) and 6N sodium hydroxide (2 ml) was heated to reflux for 5 hours. Water (50 ml) was added and the solution was acidified with concentrated hydrochloric acid (2 ml), then extracted with ethyl acetate (2×). The combined organic layers were washed with brine, dried over magnesium sulfate and concentrated to an oil (0.19 g). The product was dissolved in methanol and treated with sodium methoxide (21 mg). The solvent was removed and the solid dried (7 mg, mp 165°-169° C.).

EXAMPLE 19

(S)-2-Ethoxy-3-{2-[5-methyl-2-phenyl-4-oxazolyl)methyl]benzofuran-5-yl}propanoic acid

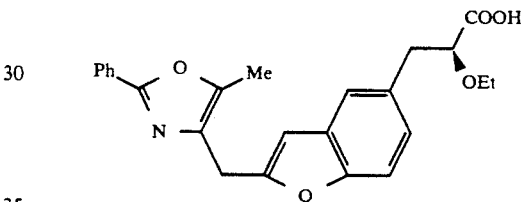

A. (S)-4-Benzyl-3-(ethoxyacetyl)oxazolidin-2-one

To a solution of (S)-4-benzyloxazolidin-2-one (4.4 g, 25 mmol) in dry tetrahydrofuran (20 ml), cooled to −78° C., was added n-butyllithium (2.5M solution in hexane, 10 ml, 25 mmol) dropwise. Another 20 ml of tetrahydrofuran was added to facilitate stirring. A solution of ethoxyacetyl chloride (3.0 g, 24 mmol) in tetrahydrofuran (5 ml) was added and the mixture was stirred at −78° C. for 30 minutes, then warmed to room temperature, poured into water and extracted with ethyl acetate (3×). The combined extracts were washed with water and brine, dried over sodium sulfate and concentrated to a yellow oil (4.3 g, $[\alpha]_D = +56.7°$).

B. 5-{(1R, 2S)-1-hydroxy-2-ethoxy-3-[(S)-4-benzyl-2-oxo-3-oxazolidinyl]-3-oxopropyl}-2-[5-methyl-2-phenyl-4-oxazolyl)methyl]benzofuran To a solution of (S)-4-benzyl-3-(ethoxyacetyl)oxazolidin-2-one (1.0 g, 3.8 mmol) in dichloromethane (10 ml), cooled to 0° C., was added freshly distilled dibutyl-boron triflate (1.1 ml, 4.6 mmol) dropwise, followed by triethylamine (0.69 ml, 4.9 mmol). After 5 minutes the solution was cooled to −78° C. and a precooled solution of 2-(5-methyl-2-phenyl-4-oxazolyl)methyl-5-benzofurancarboxaldehyde (1.33 g, 4.2 mmol) in dichloromethane (5 ml) was added. After 20 minutes the mixture was warmed to 0° C. and stirred at that temperature for 1 hour then quenched with a solution of pH 7 buffer (10 ml) in methanol (30 ml), and stirred at 0° C. for 1 hour. The mixture was then diluted with water and extracted with ethyl acetate (3×). The combined extracts were washed with brine, dried over sodium sulfate and concentrated. The product was purified by flash-chromatography (hexanes/ethyl acetate, 1:1) and obtained as a yellow solid (1.16 g, mp 66° C.).

C. 5-{(S)-2-Ethoxy-3-[(S)-4-benzyl-2-oxo-3-oxazolidinyl]-3-oxopropyl}-2-[(5-methyl-2-phenyl-4-oxazolyl)methyl]benzofuran To a solution of 5-{(1R,2S)-1-hydroxy-2-ethoxy-3-[(S)-4-benzyl-2-oxo-3-oxazolidinyl]-3-oxopropyl}-2-[(5-methyl-2-phenyl-4-oxazolyl)methyl]benzopyran (1.0 g, 1.72 mmol) in trifluoroacetic acid (20 ml) was added triethylsilane (3.0 ml, 19 mmol). The solution was stirred for 4 days at room temperature then diluted with ethyl acetate, washed with water and saturated sodium bicarbonate solution (3×), dried over sodium sulfate and concentrated. The product was isolated by flash-chromatography (hexanes/ethyl acetate, 5:1) as a pale yellow solid (0.44 g).

D. (S)-2-Ethoxy-3-{2-[(5-methyl-2-phenyl-4-oxazolyl)methyl]benzofuran-5-yl}propanoic acid 5-{(S)-2-Ethoxy-3-[(S)-4-benzyl-2-oxo-3-oxazolidinyl]-3-oxopropyl}-2-[(5-methyl-2-phenyl-4-oxazolyl)methyl]benzofuran (0.15 g, 0.26 mmol) was dissolved in tetrahydrofuran (5 ml). The solution was cooled to 0° C. and 0.5N lithium hydroxide (1.1 ml, 0.52 mmol) was added. After 15 minutes the bulk of the ethanol was removed, the residue was acidified with 1N HCl, diluted with water and extracted with ethyl acetate (3×). The combined extracts were washed with brine, dried over sodium sulfate and concentrated. The product was purified by flash-chromatography (hexanes/ethyl acetate/acetic acid, 10:10:1) then recrystallized from hexanes/ethyl acetate and obtained as a white solid (48 mg, mp 129° C., [α]$_D$ = −12.5° (c 0.99, CDCl$_3$)).

Using the appropriate reagents, the following compounds were prepared by the same procedure.

(R)-2-Ethoxy-3-{2-[(5-methyl-2-phenyl-4-oxazolyl)methyl]benzofuran-5-yl}propanoic acid (mp 129° C., [α]$_D$ = +9.3° (c 0.65, CDCl$_3$)).

(R)-3-{2-[(5-Methyl-2-phenyl-4-oxazolyl)methyl]benzofuran-5-yl}-2-phenoxypropanoic acid (mp 174°–175° C., [α]$_d$ = −13.1° (c 0.50, CDCl$_3$)).

(S)-3-{2-[(5-Methyl-2-phenyl-4-oxazolyl)methyl]benzofuran-5-yl}-2-phenoxypropanoic acid (mp 165° C., [α]$_D$ = +8.1° (c 0.07, CDCl$_3$)).

EXAMPLE 20

3-{[4-(4-Benzyloxyphenyl)ethoxy]phenyl}-2-methoxypropanoic acid

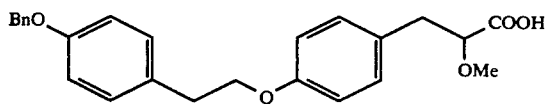

A. 1-Benzyloxy-4-(2-hydroxyethyl)benzene

To a solution of 4-hydroxyphenethyl alcohol (33 g, 0.24 mol) in dry dimethylformamide (200 ml), cooled to 0° C., was added potassium tert-butoxide (29 g, 0.26 mol) by portions. After 10 minutes, benzyl bromide (41 g, 0.28 mol) was added slowly. The reaction mixture was stirred for 15 minutes at 0° C., then for 3 hours at room temperature and was quenched with water (200 ml). The precipitate was collected, dried and recrystallized from isopropyl ether/hexanes (34 g).

B. 4-[(4-Benzyloxyphenyl)ethoxy]benzonitrile

To a suspension of sodium hydride (60%, 2.2 g, 55 mmol) in dry tetrahydrofuran (250 ml) was added a solution of 1-benzyl-oxy-4-(2-hydroxyethyl)benzene (11.4 g, 50 mmol) in tetrahydrofuran (50 ml). The reaction was heated to 40° C. for 1 hour. 4-Fluorobenzonitrile (6.7 g, 55 mmol) was added and the mixture was heated to reflux for 5 hours, cooled and neutralized with concentrated HCl. The precipitate was filtered, the filtrate was concentrated to dryness and the resulting solid was recrystallized from ethanol (12 g).

C. 4-[(4-Benzyloxyphenyl)ethoxy]benzaldehyde

4-[(4-Benzyloxyphenyl)ethoxy]benzonitrile (4.9 g, 15 mmol) was dissolved in toluene (300 ml) and treated with a 1.5M toluene solution of diisobutylaluminum hydride (10 ml, 15 mmol). The reaction mixture was stirred overnight then quenched with a saturated sodium potassium tartrate solution (100 ml). The organic layer was washed with 5% sulfuric acid (50 ml), saturated sodium bicarbonate (100 ml) and brine, dried over magnesium sulfate and concentrated to dryness. The product was purified by flash-chromatography (hexanes/ethyl acetate, 5:1) and obtained as an oil (4.0 g).

This aldehyde was converted into 2-methoxy-3-{[4-(4-benzyloxyphenyl)ethoxy]phenyl}propanoic acid (mp 65°–69° C.) by the sequence described in Example 18.

Using the appropriate reagents, the following compounds were prepared by the same procedure.

3-{[4-4-Benzyloxyphenyl)ethoxy]phenyl}-2-ethoxypropanoic acid (mp 62°–63.5° C.).

3-{[4-(4-(3-Fluorobenzyloxy)phenyl)ethoxy]phenyl}-2-methoxypropanoic acid (mp 58°–62° C.).

2-Ethoxy-3-{[4-(4-(3-fluorobenzyloxy)phenyl)ethoxy]phenyl}propanoic acid (mp 54.5°–57.5° C.).

2-Benzyloxy-3-{[4-(4-benzyloxyphenyl)ethoxy]phenyl}propanoic acid (mp 85°–86° C.).

3-[3-(5-Ethyl-2-pyridyl)propoxy]phenyl-2-methoxypropanoic acid (mp 81°–82° C.).

2-Ethoxy-3-[3-(5-ethyl-2-pyridyl)propoxy]phenylpropanoic acid (mp 80°–81° C.).

3-[3-(5-Ethyl-2-pyridyl)propoxy]phenyl-2-propoxypropanoic acid (mp 89°–90° C.).

2-Ethoxy-3-{4-[3-(5-methyl-2-phenyl-4-oxazolyl)-propanoyl]phenyl}propanoic acid (oil). $^1$H NMR (250 MNz, CDCl$_3$) δ1.11 (t, J=6.9 Hz, 3H), 2.37 (s, 3H), 2.92 (t, J=7.1 Hz, 2H), 2.94–3.09 (m, 2H), 3.13 (dd, J=13.9 Hz, 4.04 Hz, 1H), 3.35 (t, J=7.1 Hz, 3H), 3.60 (m, 1H), 3.61 (dd, J=9.1 Hz, 7.0 Hz, 1H), 7.32 (d, J=8.3 Hz, 2H), 7.36–7.44 (m, 3H), 7.89 (d, J=8.3 Hz, 2H), 7.94–7.98 (m, 2H), 8.95 (br, s, 1H).

EXAMPLE 21

3-[2-(4-Benzyloxybenzyl)benzofuran-5-yl]-2-ethoxypropanoic acid

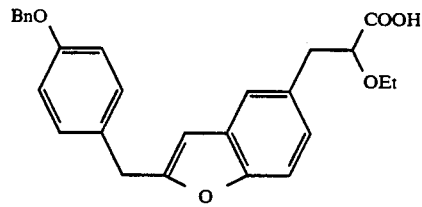

A. 5-Bromo-2-(4-benzyloxybenzoyl)benzofuran

5-Bromosalicylaldehyde (2.9 g, 14.5 mmol), cesium carbonate (2.5 g, 7.7 mmol) and acetonitrile (40 ml) were combined and heated to reflux for 30 minutes. The mixture was cooled to 0° C. and a solution of 4'-benzyloxy-2-bromoacetophenone (J. Het. Chem., 2, 310

(1965)) (4.7 g, 15 mmol) in acetonitrile (20 ml) was added. The cooling bath was removed, the mixture stirred at room temperature for 2.5 hours and the precipitate collected (4.5 g).

B. 5-Bromo-2-(4-benzyloxybenzyl)benzofuran

5-Bromo-2-(4-benzyloxybenzoyl)benzofuran (9.0 g, 22 mmol), sodium cyanoborohydride (10.4 g, 0.17 mol), zinc iodide (10.5 g, 0.35 mol) and 1,2-dichloroethane (350 ml) were combined and heated to reflux for 6 hours. The mixture was cooled, quenched with saturated ammonium chloride (500 ml), acidified with concentrated HCl and stirred for 30 minutes. The layers were separated, the aqueous layer was extracted with dichloromethane (400 ml) and the combined organic layers were washed with water and brine, dried over magnesium sulfate and concentrated, leaving a white solid (8.5 g).

C. 2-(4-Benzyloxybenzyl)-5-cyanobenzofuran

A mixture of 5-bromo-2-(4-benzyloxybenzyl)benzofuran (4.4 g, 11 mmol), copper cyanide (1.50 g, 17 mmol) and bis(triphenylphosphine) palladium (II) chloride (0.79 g, 1.1 mmol) in DMF (40 ml) was heated to reflux overnight. The mixture was cooled, ethyl acetate (200 ml) and concentrated ammonium hydroxide (100 ml) were added. The organic layer was washed with water (3×) and brine, dried over magnesium sulfate and concentrated. The product was purified by flash chromatography (hexanes/ethyl acetate, 5:1) and obtained as a solid (2.6 g, mp 131.5°-132.5° C.). This compound was transformed into the corresponding aldehyde as in Example 20 and into 3-[2-(4-benzyloxybenzyl)benzofuran-5-yl]-2-ethoxypropanoic acid (mp 91°-94° C.) by the sequence described in Example 18.

The following compounds were prepared by the same sequence from the appropriate starting materials and reagents.

3-[2-(4-Benzyloxybenxzyl)benzofuran-5-yl]-2-methoxypropanoic acid (mp 98°-100° C.).

2-Benzyloxy-3-[2-(4-benzyloxybenzyl)benzofuran-5-yl]propanoic acid (mp 115°-116.5° C.).

EXAMPLE 22

(S)-3,4-Dihydro-2-ethoxy-3-{(R)-2-[4-(3-fluorobenzyloxy)benzyl]-2H-benzopyran-6-yl}propanoic acid

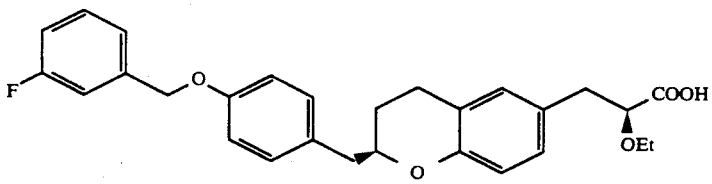

A. (R)-(−)-3,4-Dihydro-2-(4-methoxybenzyl)-2H-benzopyran (R)-(−)-3,4-Dihydro-2-trifluoromethane-sulfonyloxymethyl-2H-benzopyran(23.0 g, 78 mmol) and copper (I) bromide dimethyl sulfide complex (2.8 g, 12 mmol) were dissolved in tetrahydrofuran (400 ml) under a nitrogen atmosphere and cooled to −10° C. 4-Anisyl-magnesium bromide (215 ml of a 1M solution in tetrahydrofuran, 0.215 mol) was added dropwise over 30 minutes, keeping the temperature below −5° C. The solution was stirred for 3 hours at 0° C. and then slowly poured into a mixture of water (800 ml) containing ammonium chloride (96 g, 1.8 mol) and methylene chloride (400 ml). The layers were separated and the aqueous portion was extracted with methylene chloride (400 ml). The combined organics were washed with 10% ammonium chloride (2×400 ml), water (250 ml), and brine (250 ml). The methylene chloride layer was dried (MgSO₄), filtered and concentrated in vacuo. The residue was purified on silica gel using hexanes/methylene chloride (1:1 as eluent to afford 18.5 g (92% yield of the title product as an oil. [α]$_D$−99.2° (c 1.7, MeOH); ¹H NMR (300 MHz, CLCl₃) δ1.6–1.7 (m, 1H), 1.9–2.0 (m, 1H), 2.7–2.8 (m, 3H), 3.1 (dd, 1H), 3.8 (s, 3H), 4.1 (m, 1H), 6.8 (m, 3H), 7.0 (m, 2H), 7.2 (m, 2H).

B. (R)-(−)-3,4-Dihydro-2-(4-hydroxybenzyl)-2H-benzopyran (R)-(−)-3,4-Dihydro-2-(4-methoxybenzyl)-2H-benzopyran (812 mg, 3.2 mmol), and lithium iodide (750 mg, 5.6 mmol) were dissolved in 2,4,6-collidine (2 ml) and heated to reflux for 24 hours. The reaction mixture was cooled, diluted with ethyl acetate (20 ml) and 10% HCl (20 ml), and stirred for 10 minutes. The layers were separated and the aqueous portion was extracted with ethyl acetate (50 ml). The combined organics were washed with water (20 ml), brine (20 ml), and were dried MgSO₄). The solvent was removed in vacuo and the residue purified on silica gel using hexanes/ethyl acetate (3:1) as eluent to afford 730 mg of a colorless oil which crystallized upon standing, mp 60°-62°. C.; [α]$_D$−110.2° (c 1.0, MeOH); ¹H NMR (300 MHz, CDCl₃) δ1.7 (m, 1H), 2.0 (m, 1H), 2.7–2.8 (m, 3H), 3.1 (dd, 1H), 4.2 (m, 1H), 6.8 (m, 3H), 7.0–7.2 (m, 4H).

C. (R)-(−)-2-(4-Acetoxybenzyl)-3,4-dihydro-2-benzopyran (R)-(−)-2-(4-Dihydro-2-hydroxybenzyl)-2H-benzopyran (5.0 g, 20 mmol), 4-dimethylaminopyridine (240 mg, 2 mmol), triethylamine (2.6 g, 25 mmol) and acetic anhydride (2.9 g, 28 mmol) were dissolved in methylene chloride (75 ml) and stirred at room temperature for 2 hours under a nitrogen atmosphere. The solvent was removed in vacuo and the residue purified on silica gel using hexanes/ethyl acetate (3:1) as eluent to afford an oil which was crystallized from hexanes to yield 4.0 g of the title product, mp 64°-65° C.; [α]$_D$−98.9° (c 1.3, MeOH); ¹H NMR (300 MHz, CLCl₃) δ1.7 (m, 1H), 1.9 (m, 1H), 2.3 (s, 3H), 2.7 (m, 2H), 2.8 (dd, 1H), 3.1 (m, 1H), 4.2 (m, 1H), 6.8 (m, 2H), 7.0 (m, 3H), 7.2 (m, 2H).

D. (R)-(−)-2-(4-Acetoxybenzyl)-3,4-dihydro-6-formyl-2H-benzopyran (R)-(−)-2-(4-Acetoxybenzyl)-3,4-dihydro-2H-benzopyran (16.6 g, 59 mmol), N-methylformanilide (23.9 g, 0.177 mol), and phosphorous oxychloride (18.0 g, 0.118 mol) were heated to 90° C. for 3 hours under a nitrogen atmosphere. The reaction mixture was cooled and poured into ice water (250 ml). The aqueous solution was extracted with ethyl acetate (2×500 ml) and the combined organics were washed with saturated NaHCO₃ (250 ml), water (250 ml), brine (250 ml), and dried (MgSO₄). The solvent was removed in vacuo and the residue purified on silica gel using hexanes/ethyl acetate (3:1) as eluent to afford 15.7 g (86% yield) of the 6-formyl derivative, ¹H NMR (300 MHz CDCl₃) δ1.8

(m, 1H), 2.1 (m, 1H), 2.3 (s, 3H), 2.8 (m, 2H), 2.9 (m, 1H), 3.1 (m, 1H), 4.3 (m, 1H), 6.9 (d, 1H), 7.0 (d, 2H), 7.3 (d, 2H), 7.6 (m, 2H), 9.8 (s, 1H).

E. (R)-(−)-3,4-Dihydro-6-formyl-2-(4-hydroxybenzyl)-2H-benzopyran (R)-(−)-2-(4-Acetoxybenzyl)-3,4-dihydro-6-formyl-2H-benzopyran (15.7 g, 51 mmol) was dissolved in a mixture of methanol (200 ml), tetrahydrofuran (200 ml) and 2M NaOH (200 ml) and stirred at room temperature for 2 hours. The reaction mixture was concentrated in vacuo, diluted with water (100 ml) and acidified with 10% HCl (250 ml). The aqueous solution was extracted with ethyl acetate (2×500 ml) and the combined organics were washed with water (250 ml), brine (250 ml), and dried (MgSO4). The solvent was removed in vacuo and the residue was crystallized from hexanes/ethyl acetate (3:1) to afford 10.1 g of the title compound, mp 134°-135° C.; [α]$_D$−155.2° (c 1.0, MeOH); $^1$H NMR (300 MHz CDCl3) δ1.6 (m, 1H), 1.9 (m, 1H), 2.8 (m, 3H), 3.0 (dd, 1H), 4.2 (m, 1H), 5.1 (br s, 1H, OH), 6.7 (d, 2H), 6.8 (d, 1H), 7.0 (d, 2H), 7.5 (m, 2H), 9.7 (s, 1H).

F. (R)-2-[4-(3-Fluorobenzyloxy)benzyl]-3,4-dihydro-6-formyl-2H-benzopyran

To a solution of (R)-3,4-dihydro-6-formyl-2-(4-hydroxybenzyl)-2H-benzopyran (1.8 g, 6.7 mmol) in DMF (10 ml) at 0° C. was added potassium tert-butoxide (0.83 g, 7.4 mmol). After 30 minutes m-fluorobenzyl bromide (0.91 ml), 7.4 mmol) was added and the resulting slurry was warmed to room temperature and stirred for 2 hours. Water was added and the precipitate was collected, washed with water and air dried (2.5 g).

G. (R)-6-{(1R,2S)-1-Hydroxy-2-ethoxy-3-[(S)-4-benzyl-2-oxo-3-oxazolidinyl]-3-oxopropyl}-2-[4-(3-fluorobenzyloxy}benzyl]-2H-benzopyran Trifluoromethanesulfonic acid (0.64 ml, 7.2 mmol) was added to a 1M solution of triethylborane in toluene (7.2 ml, 7.2 mmol) and the mixture was heated to 40° C. for 1 hour then cooled to 0° C. A solution of (S)-4-benzyl-3-(ethoxyacetyl)oxazolidin-2-one (Example 19) (0.64 g, 3.6 mmol) in dichloromethane (5 ml) was added, followed by diisopropylethylamine (1.33 ml, 7.6 mmol). After 30 minutes the solution was cooled to −78° C. and a solution of (R)-2-[4-(3-fluorobenzyloxy)benzyl]-3,4-dihydro-6-formyl-2H-benzopyran (1.0 g, 3.6 mmol) in dichloromethane (15 ml) was added. The mixture was stirred at −78° C. for 2 hours then 30 minutes at 0° C. and quenched with pH 7 buffer (5 ml). The mixture was diluted with ether, the organic layer was washed with water and brine, dried over magnesium sulfate and concentrated. The product was isolated by flash-chromatography (hexanes/ethyl acetate, 3:2) as an oil (85 mg).

H. (R)-6-{(S)-2-Ethoxy-3-[(S)-4-benzyl-2-oxo-3-oxazolidinyl]-3-oxopropyl}-2-[4-(3-fluorobenzyloxy)-benzyl]-2H-benzopyran (R)-6-{(1R,2S)-1-Hydroxy-2-ethoxy-3-[(S)-4-benzyl-2-oxo-3-oxazolidinyl]-3-oxopropyl}-2-[4-(3-fluorobenzyloxy)benzyl]-2H-benzopyran (80 mg, 0.13 mmol) was dissolved in trifluoroacetic acid (2 ml) and triethylsilane (0.20 ml) was added. After 30 minutes the solution was diluted with ether, washed with water (2×) and saturated sodium bicarbonate (2×), dried over magnesium sulfate and concentrated. The product was purified by flash-chromatography (hexanes/ethyl acetate, 2:1) and obtained as an oil (39 mg).

I. (S)-2-Ethoxy-3-{(2R)-2-[4-(3-fluorobenzyloxy)benzyl]-3,4-dihydro-2H-benzopyran-6-yl}propanoic acid (R)-6-{(S)-2-Ethoxy-3-[(S)-4-benzyl-2-oxo-3-oxazolidinyl]-3-oxopropyl}-2-[4-(3-fluorobenzyloxy)-benzyl]-2H-benzopyran (39 mg, 63 mmol) was dissolved in tetrahydrofuran (1.5 ml) at 0° C. and treated with 0.5N lithium hydroxide (1 ml). The reaction mixture was warmed to room temperature and stirred for 1 hour, then acidified with 1N hydrochloric acid and extracted with ethyl acetate (3×). The combined extracts were washed with water and brine, dried over magnesium sulfate and concentrated. The product was purified by flash-chromatography (hexanes/ethyl acetate/acetic acid, 15:5:1) and isolated as an oil (30 mg). $^1$H NMR (300 MHz, CDCl3) δ1.16 (t, J=6.9 Hz, 3H), 1.67 (m, 1H), 1.93 (m, 1H), 2.68-2.72 (m, 2H), 2.79 (dd, J=13.8 Hz, 6.9 Hz, 1H), 2.88 (dd, J=14.4 Hz, 7.7 Hz, 1H), 3.00 (dd, J=12.2 Hz, 4.3 Hz, 1H), 3.05 (dd, J=13.4 Hz, 7.6 Hz, 1H), 3.43 (m, 1H), 3.58 (m, 1H), 4.01 (dd, J=7.5 Hz, 4.2 Hz, 1H), 4.12 (m, 1H), 5.03 (s, 2H), 6.71 (d, J=8.2 Hz, 1H), 6.88-7.02 (m, 3H), 6.89 (d, J=8.5 Hz, 2H), 7.12-7.18 (m, 2H), 7.17 (d, J=8.6 Hz, 2H), 7.32 (m, 1H).

The following compounds were prepared from the corresponding aldehydes (example 20) by the same sequence.

(S) Sodium 2-ethoxy-3-{[4-(4-(3-fluorobenzyloxy)-phenyl)ethoxy]phenyl}propanoate (mp 195°-200° C.).

(R) Sodium 2-ethoxy-3-{[4-(4-(3-fluorobenzyloxy)-phenyl)ethoxy]phenyl}propanoate (mp 200°-205° C.).

EXAMPLE 23

Sodium 3,4-dihydro-2-ethoxy-3-[(R)-2-(4-benzyloxybenzyl)-2H-benzopyran-6-yl]propanoate

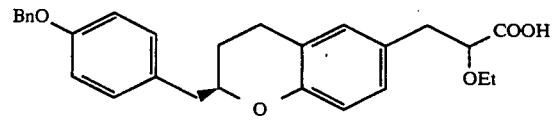

(R)-(−)-3,4-Dihydro-6-formyl-2-(4-hydroxybenzyl)-2H-benzopyran (Example 22) was transformed into the title compound by a sequence analogous to the one described in Example 18, mp 160°-170° C. (dec.).

Using the corresponding reagent, 3,4-dihydro-2-ethoxy-3-{(R)-2-[4-(5-ethyl-2-pyridyl)methoxy]-2H-benzopyran-6-yl}propanoate was prepared by the same method, mp 108°-109° C.

EXAMPLE 24

Sodium, 3,4-dihydro-2-ethoxy-3-[(R)-2-benzyl-2H-benzopyran-y-yl]propanoate

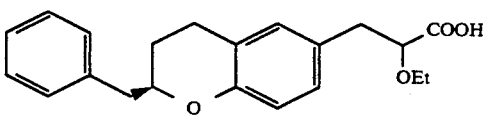

(R)-(−)-3,4-Dihydro-6-formyl-2-benzyl-2H-benzopyran was prepared from (R)-(−)-3,4-dihydro-2-trifluoromethanesulfonyloxymethyl-2H-benzopyran and phenylmagnesium bromide as described in Example 22 and converted to the title compound as in Example 18 (foam). $^1$H NMR (300 MHz, CDCl3) δ1.2 (t, 3H), 1.7 (m, 1H), 2.0 (m, 1H), 2.8-3.1 (m, 6H), 3.4 (m, 1H), 3.6

(m, 1H), 4.0 (dd, 1H), 4.1 (m, 1H), 6.7 (d, 2H), 6.9 (s, 1H), 6.95 (dd, 1H), 7.2 (m, 5H).

EXAMPLE 25

2-Phenoxy-3-[4-(2-phenyl)ethoxyphenyl]propanoic acid

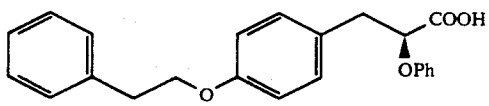

A. (S)-4-Benzyl-3-[(1S),(2R)-2-(4-benzyloxyphenyl)-2-hydroxy-1-phenoxyethyl]-2-oxazolidinone Trifluoromethanesulfonic acid (5.0 ml, 56 mmol) was added to a solution of triethylborane in hexanes (56 ml of a 1M solution, 56 mmol). After the bubbling stopped, the solution was heated to 40° C. for 1 hour then cooled to 0° C., a solution of (S)-4-benzyl-3-(phenoxyacetyl)oxazolidin-2-one (prepared as in Example 19) (5.0 g, 28 mmol) in dichloromethane (90 ml) was added followed by diisopropylethylamine (12.3 ml, 71 mmol) dropwise. After 30 minutes the solution was cooled to −78° C. and treated with a solution of 4-benzyloxybenzaldehyde (6.0 g, 28 mmol) in dichloromethane (80 ml). After 2 hours at −78° C., the solution was warmed to 0° C., stirred for 30 minutes and quenched with Ph 7 buffer. The layers were separated, the aqueous portion was extracted with dichloromethane, the combined extracts were washed with water and brine, dried over magnesium sulfate and concentrated. The product was isolated by flash-chromatography (hexanes/ethyl acetate, 1:1) as an oil (6.5 g).

B. (S)-4-Benzyl-3-[(1S)-2-(4-benzyloxyphenyl)-1-phenoxyethyl]-2-oxazolidinone

Triethylsilane (20 ml, 125 mmol) was added dropwise to a solution of (S)-4-benzyl-3-[(1S),(2R)-2-(4-benzyloxyphenyl)-2-hydroxy-1-phenoxy-ethyl]-2-oxazolidinone (6.5 g, 12.4 mmol). The solution was stirred for 1 hour then was diluted with ether, washed with water (2×), saturated sodium bicarbonate (2×, carefully), dried over magnesium sulfate and concentrated. The product was isolated by flash-chromatography (hexanes/ethyl acetate, 4:1) as an oil (1.8 g).

C. (S)-4-Benzyl-3-[(1S)-2-(4-hydroxyphenyl)-1-phenoxyethyl]-2-oxazolidinone

A solution of (S)-4-benzyl-3-[(1S)-2-(4-benzyloxyphenyl)-1-phenoxyethyl]-2-oxazolidinone (1.8 g) in ethyl acetate (50 ml) containing 10% palladium on carbon (1.8 g) was hydrogenated at 40 psi overnight. The catalyst was filtered, the solution concentrated and the product purified by flash-chromatography (hexanes-/ethyl acetate, 3:2) as an oil (0.81 g).

D. (S)-4-Benzyl-3-{(1S)-2-[4-(2-phenylethoxy)-phenyl]-1-phenoxyethyl}-2-oxazolidinone To a solution of (S)-4-benzyl-3-[(1S)-2-(4-hydroxyphenyl)-1-phenoxyethyl]-2-oxazolidinone (0.25 g, 0.60 mmol), phenethyl alcohol (80 ml, 0.66 mmol) and triphenylphosphine (0.17 g, 0.66 mmol) in tetrahydrofuran (5 ml) was added diisopropylazodicarboxylate (0.13 ml, 0.66 mmol). The mixture was stirred overnight in the dark, then concentrated. The product was isolated by flash-chromatography (hexanes/ethyl acetate, 3:1) as a white solid (0.28 g).

E. 2-Phenoxy-3-[4-(2-phenyl)ethoxyphenyl]-propanoic acid

A solution of (S)-4-benzyl-3-{(1S)-2-[4-(2-phenylethoxy)phenyl]-1-phenoxyethyl}-2-oxazolidinone (0.28 g, 0.54 mmol) in tetrahydrofuran (10 ml) and 0.5N lithium hydroxide (5 ml) was stirred at 0° C. for 3 hours. The mixture was acidified with 1N HCl, diluted with water and extracted with ethyl acetate (3×). The combined extracts were washed with brine, dried over magnesium sulfate and concentrated. The product was isolated by flash chromatography (hexanes/ethyl acetate/acetic acid, 15:5:1) as a white solid, mp 96°–97° C. [α]$_D$ −1.0° (c 1.76, CHCl$_3$).

The following compounds were prepared by the same sequence from the appropriate starting materials and reagents.

(S)-3-{4-[2-(2-Aminophenyl)]ethoxyphenyl}-2-phenoxy-propanoic acid, mp 100°–103° C. [α]$_D$ −9.7° (c 1.17, CHCl$_3$).

(S)-3-{4-[2-(4-Benzyloxyphenyl)]ethoxyphenyl}-2-phenoxypropanoic acid, mp 103°–105° C. [α]$_D$ +7.60° (c 1.13, CDCl$_3$).

(R)-3-{4-[2-(4-Benzyloxyphenyl)]ethoxyphenyl}-2-phenoxypropanoic acid, mp 103°–105° C. [α]$_D$ −8.16° (c 1.93, CDCl$_3$).

(S)-3-{4-[2-(4-Benzyloxyphenyl)]ethoxyphenyl}-2-ethoxypropanoic acid (oil). [α]$_D$ +5.82° (c 0.55, CDCl$_3$).

EXAMPLE 26

2-Ethoxy-3-(2-benzyl-5-benzoxazolyl)propanoic acid

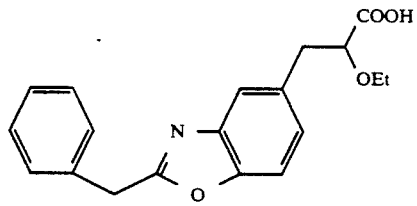

A. 3-(4-Benzyloxy-3-nitrophenyl)-2-ethoxypropanenitrile

This compound was prepared in 3 steps from 4-benzyloxy-3-nitrobenzaldehyde according to the procedure described in Example 18.

B. 3-(3-Amino-4-hydroxyphenyl)-2-ethoxypropanenitrile

A solution of 3-(4-benzyloxy-3-nitrophenyl)-2-ethoxypropanenitrile (0.54 g, 1.7 mmol) in ethanol (25 ml) and acetic acid (75 ml) containing 10% palladium on carbon (0.40 g) was hydrogenated at 45 psi for 1 hour. The catalyst was filtered and the solution concentrated. The residue was treated with 5% sodium bicarbonate (100 ml) and extracted with ethyl acetate (3×100 ml). The combined extracts were washed with water (2×100 ml) and brine (100 ml), dried over sodium sulfate and concentrated. The product was isolated by column chromatography (silica gel, 2% methanol in chloroform) as a solid (0.20 g, mp 114°–115° C.).

C. 2-Ethoxy-3-(4-hydroxyphenyl-3-benzamido)-propanenitrile

A mixture of 3-(3-amino-4-hydroxyphenyl)-2-ethoxypropanenitrile (0.26 g, 1.2 mmol), phenylacetic acid (0.17 g, 1.2 mmol) and dicyclohexylcarbodiimide (0.25 g, 1.2 mmol) in dimethylformamide (0.5 ml) and tetrahydrofuran (15 ml) was stirred at room temperature for 14 hours. The solution was concentrated, the residue taken up in ethyl acetate (75 ml), this mixture was filtered and the filtrate was washed with water (3×25 ml) and brine (25 ml), dried over sodium sulfate and concentrated. The product was isolated by column chromatography (silica gel, chloroform) as an oil (0.21 g).

D. 2-Ethoxy-3-(2-benzyl-5-benzoxazolyl)propanenitrile

A solution of 2-ethoxy-3-(4-hydroxyphenyl-3-benzamido)propanenitrile (83 mg, 0.26 mmol) and pyridinium p-toluenesulfonate (15 mg, 63 mmol) in xylenes (10 ml) was heated to reflux for 9 hours, then cooled, diluted with ethyl acetate (65 ml), washed with water (3×25 ml) and brine (25 ml), dried over sodium sulfate and concentrated. The product was isolated by column chromatography (silica gel, chloroform) as a yellow oil that solidified on standing (50 mg).

E. 2-Ethoxy-3-(2-benzyl-5-benzoxazolyl)propanoic acid

2-Ethoxy-3-(2-benzyl-5-benzoxazolyl)propanenitrile was hydrolyzed as described in Example 18.

HRMS: Calc. 325.1314 Found 325.1288

The following compounds were prepared by the same sequence from the appropriate starting materials and reagents.

3-[2-(4-Benzyloxybenzyl)-5-benzoxazoly]-2-ethoxypropanoic acid.

HRMS: Calc. 431.1738 Found 431.1732

2-Ethoxy-3-[2-(5-methyl-2-phenyl-4-oxazolylmethyl)-5-benzoxazolyl]propanoic acid.

HRMS: Calc. 406.1533 Found 406.1528

2-Ethoxy-3-[2-(2-pyridylmethyl)-5-benzoxazolyl]-propanoic acid.

HRMS: Calcd. 326.1270 Found 326.1266

I claim:

1. A method of lowering blood pressure in a mammal in need of such treatment which comprises administering to said mammal a blood pressure lowering effective amount of a compound of the formula

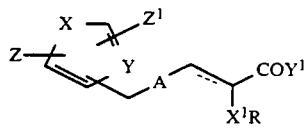

wherein:
A is

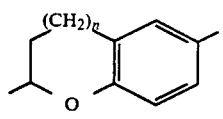

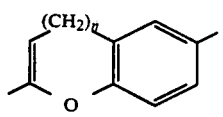

or

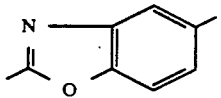

n is 0 or 1;
---- represents a bond or no bond;
R is $C_1$ to $C_8$ alkyl, $C_3$ to $C_7$ cycloalkyl, $C_3$ to $C_8$ alkenyl, $C_3$ to $C_8$ alkynyl, phenyl, $C_7$ to $C_8$ phenylalkyl, $C_2$ to $C_8$ alkanoyl, or one of said groups mono- or disubstituted with $C_1$ to $C_3$ alkyl, trifluoromethyl, hydroxy, $C_1$ to $C_3$ alkoxy, fluoro or chloro;

X is S, O, $NR^2$, —CH=CH—, —CH=N— or —N=CH—;

$R^2$ is hydrogen, $C_1$ to $C_3$ alkyl, phenyl or benzyl;

Y is CH or N;

Z is hydrogen, $C_1$ to $C_7$ alkyl, $C_3$ to $C_7$ cycloalkyl, phenyl, or phenyl mono- or disubstituted with $C_1$ to $C_3$ alkyl, trifluoromethyl, $C_1$ to $C_3$ alkoxy, phenyl, phenoxy, benzyl, benzyloxy, fluoro or chloro;

$X^1$ is O, S, SO or $SO_2$;

$Y^1$ is hydroxy, $C_1$ to $C_3$ alkoxy, phenoxy, benzyloxy, amino, $C_1$ to $C_4$ alkanoylamino, $C_1$ to $C_4$ alkanesulfonylamino, benzenesulfonylamino, naphthalenesulfonylamino, di($C_1$ to $C_3$ alkyl)aminosulfonylamino, or one of said groups mono- or disubstituted with $C_1$ to $C_3$ alkyl, trifluoromethyl, hydroxy, $C_1$ to $C_3$ alkoxy, fluoro or chloro; and $Z^1$ is hydrogen or $C_1$ to $C_3$ alkyl;

a pharmaceutically acceptable cationic salt thereof when $Y^1$ is hydroxy; or a pharmaceutically acceptable acid addition salt thereof when the compound contains a basic nitrogen atom.

2. A method according to claim 1 wherein ---- represents no bond and $X^1$ is 0.

3. A method according to claim 2 wherein A is

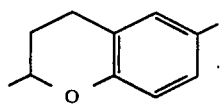

4. A method according to claim 3 wherein X is —CH=CH—, Y is —CH—, R is ethyl and $Y^1$ is hydrogen.

5. A method according to claim 4 wherein Z and $Z^1$ are both hydrogen.

6. The method according to claim 5 comprising administering

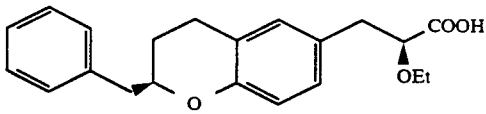

7. A method according to claim 4 wherein $Z^1$ is hydrogen and Z is 4-benzyloxy.

8. The method according to claim 7 comprising administering

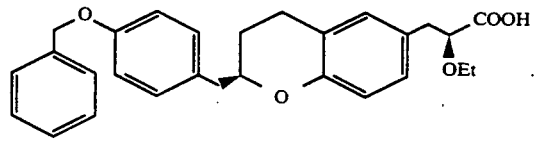

9. A method of lowering blood pressure in a mammal suffering from hypertension comprising administering to said mammal a blood pressure lowering effective amount of a compound of the formula

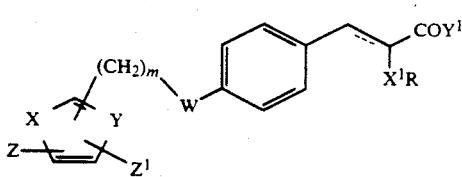

wherein

---- represents a bond or no bond;

R is $(C_1-C_8)$alkyl, $(C_3-C_7)$alkenyl, $(C_3-C_8)$alkynyl, phenyl, $(C_7-C_8)$phenylalkyl, $(C_2-C_8)$alkanoyl, or one of said groups mono- or disubstituted with $(C_1-C_3)$alkyl, trifluoromethyl, hydroxy, $(C_1-C_3)$alkoxy, fluoro or chloro;

W is O, CO, $CH_2$, CHOH or —CH=CH—;

m is 0, 1 or 2;

X is S, O, $NR^2$, —CH=CH—, —CH=N— or —N=CH—;

$R^2$ is hydrogen, $(C_1-C_3)$alkyl, phenyl or benzyl;

Y is CH or N;

Z is hydrogen, $(C_1-C_7)$alkyl, $(C_3-C_7)$cycloalkyl, phenyl, or phenyl mono- or disubstituted with $(C_1-C_3)$alkyl, trifluoromethyl, $(C_1-C_3)$alkoxy, phenyl, phenoxy, benzyl, benzyloxy, fluoro or chloro;

$Z^1$ is hydrogen or $(C_1-C_3)$alkyl;

$X^1$ is O, S, SO or $SO_2$; and $Y^1$ is hydroxy, $(C_1-C_3)$alkoxy, phenoxy, benzyloxy, amino, $(C_1-C_4)$alkanoylamino, $(C_1-C_4)$alkanesulfonylamino, benzenesulfonylamino, napthalenesulfonylamino, di[$(C_1-C_3)$alkyl]aminosulfonylamino, or one of said groups mono- or disubstituted with $(C_1-C_3)$alkyl, trifluoromethyl, hydroxy $(C_1-C_3)$alkoxy, fluoro or chloro;

a pharmaceutically-acceptable cationic salt thereof when $Y^1$ is hydroxy; or a pharmaceutically-acceptable acid addition salt thereof when the compound contains a basic nitrogen atom.

10. A method according to claim 9 wherein m is 2, W is O, X is —CH=CH— and Y is —CH—.

11. A method according to claim 10 wherein $X^1$ is O, R is ethyl and $Y^1$ is hydrogen.

12. A method according to claim 11 wherein $Z^1$ is hydrogen and Z is

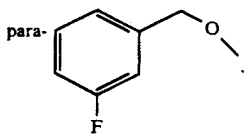

13. The method according to claim 12 comprising administering

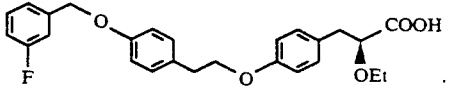

* * * * *